United States Patent [19]

Spolyar

[11] Patent Number: 4,579,117
[45] Date of Patent: Apr. 1, 1986

[54] PORTABLE ROENTGENOGRAPHIC CEPHALOSTAT

[76] Inventor: John L. Spolyar, 2769 Homewood Dr., Troy, Mich. 48098

[21] Appl. No.: 563,648

[22] Filed: Dec. 20, 1983

Related U.S. Application Data

[63] Continuation-in-part of Ser. No. 453,949, Dec. 28, 1982.

[51] Int. Cl.⁴ ............................................. G03B 41/16
[52] U.S. Cl. ................................ 128/303 B; 378/180; 378/178
[58] Field of Search .............. 128/303 B, 653; 378/20, 378/79, 81, 177, 178, 179, 180, 208, 162, 163

[56] References Cited

U.S. PATENT DOCUMENTS

| | | | |
|---|---|---|---|
| 2,032,833 | 3/1936 | Broadbent | 250/34 |
| 2,254,544 | 9/1941 | Plotz et al. | 250/50 |
| 3,025,397 | 3/1962 | Travis et al. | 250/50 |
| 3,072,788 | 1/1963 | Oller | 378/178 X |
| 3,293,430 | 12/1966 | Wustner | 250/66 |
| 3,364,352 | 1/1968 | Fry et al. | 250/50 |
| 3,514,606 | 5/1970 | Rabey | 378/180 X |
| 3,626,186 | 12/1971 | Allard | 378/178 X |
| 3,633,028 | 1/1972 | Marino | 250/50 |
| 3,704,707 | 12/1972 | Halloran | 378/162 X |
| 3,737,660 | 6/1973 | Ando et al. | 250/50 |
| 3,790,803 | 2/1974 | Phillips | 250/50 |
| 3,875,412 | 1/1975 | Hozumi | 250/491 |
| 3,916,207 | 10/1975 | Reed | 250/444 |
| 4,088,893 | 5/1978 | Schroeder | 378/180 X |
| 4,144,460 | 3/1979 | Norman | 378/180 X |
| 4,229,656 | 10/1980 | Iversen et al. | 378/178 |
| 4,256,112 | 3/1981 | Kopf et al. | 128/303 B |
| 4,341,220 | 7/1982 | Perry | 128/303 B |

Primary Examiner—Edward M. Coven
Attorney, Agent, or Firm—Lon H. Romanski

[57] ABSTRACT

A portable cephalostat is shown as having a frame-like base subassembly which provides for an area upon which a patient's head is to rest and a support for supporting locating arms which serve to locate the patient's head in a selected position; the base subassembly provides for the placement of a first film, to be exposed, below the patient's head and for the placement of additional film, also to be exposed, generally to one side of the patient's head and generally parallel to and spaced a first distance from the mid-sagittal plane of the patient's head; provision is also made for the placement of other film, also to be exposed, generally to the same one side of the patient's head and generally parallel to and spaced a second distance from the mid-sagittal plane of the patient's head; further provision is made for the placement of still further additional film, to be exposed, generally transverse to the patient's head and spaced from the top thereof; an indicator is provided for, upon attaining the desired location of the patient's head, automatically indicating the elevation of the axis of the patient's auditory canals with respect to the first film; certain elements are made to be foldable to conserve space and assist in the transportation of the cephalostat; the cephalostat is also provided with adaptive structure enabling the detachable attachment thereto of aiming apparatus whereby either intermittent or panoramic X-ray exposures of a certain portion of the patient's head can be made.

31 Claims, 41 Drawing Figures

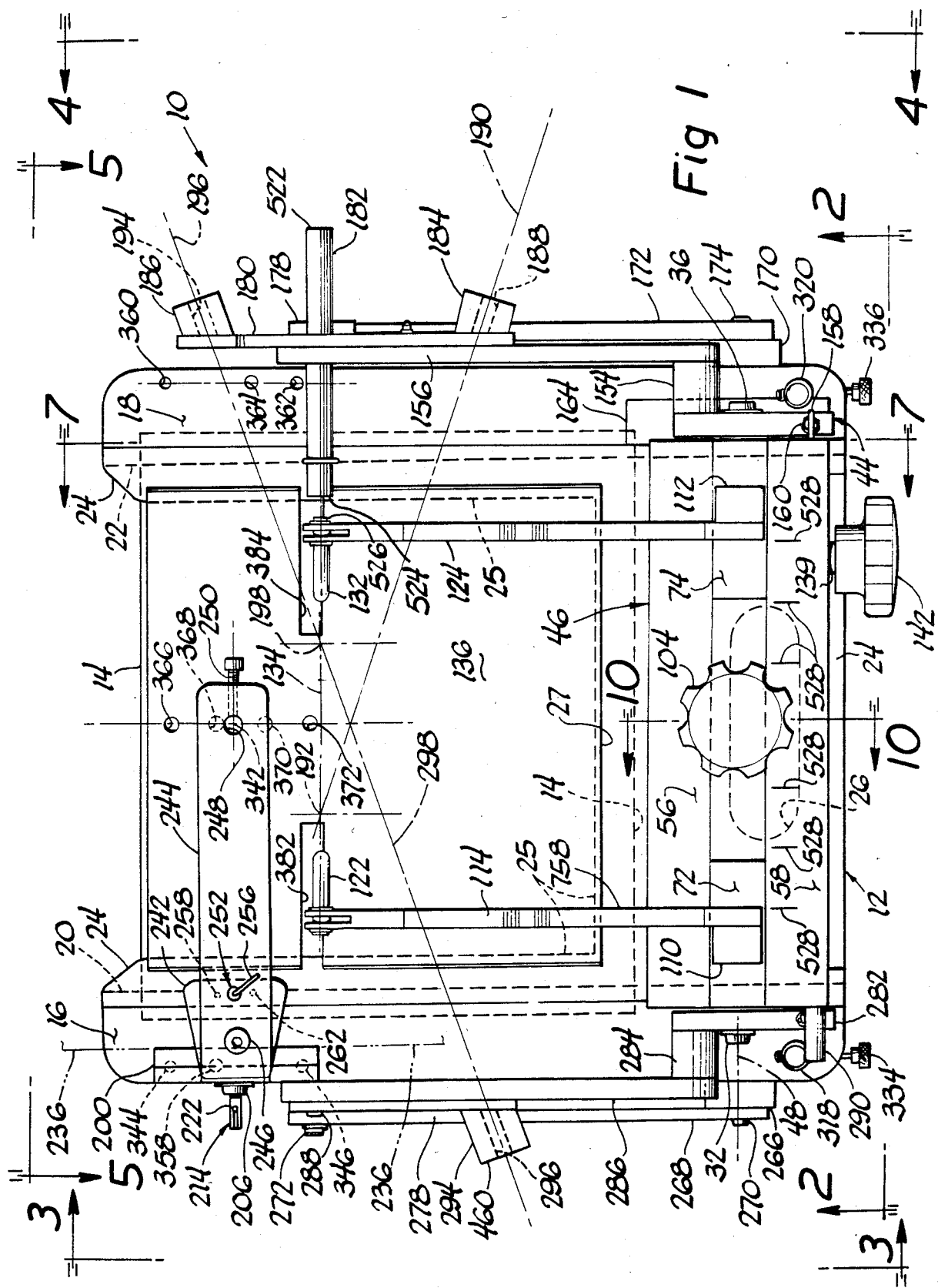

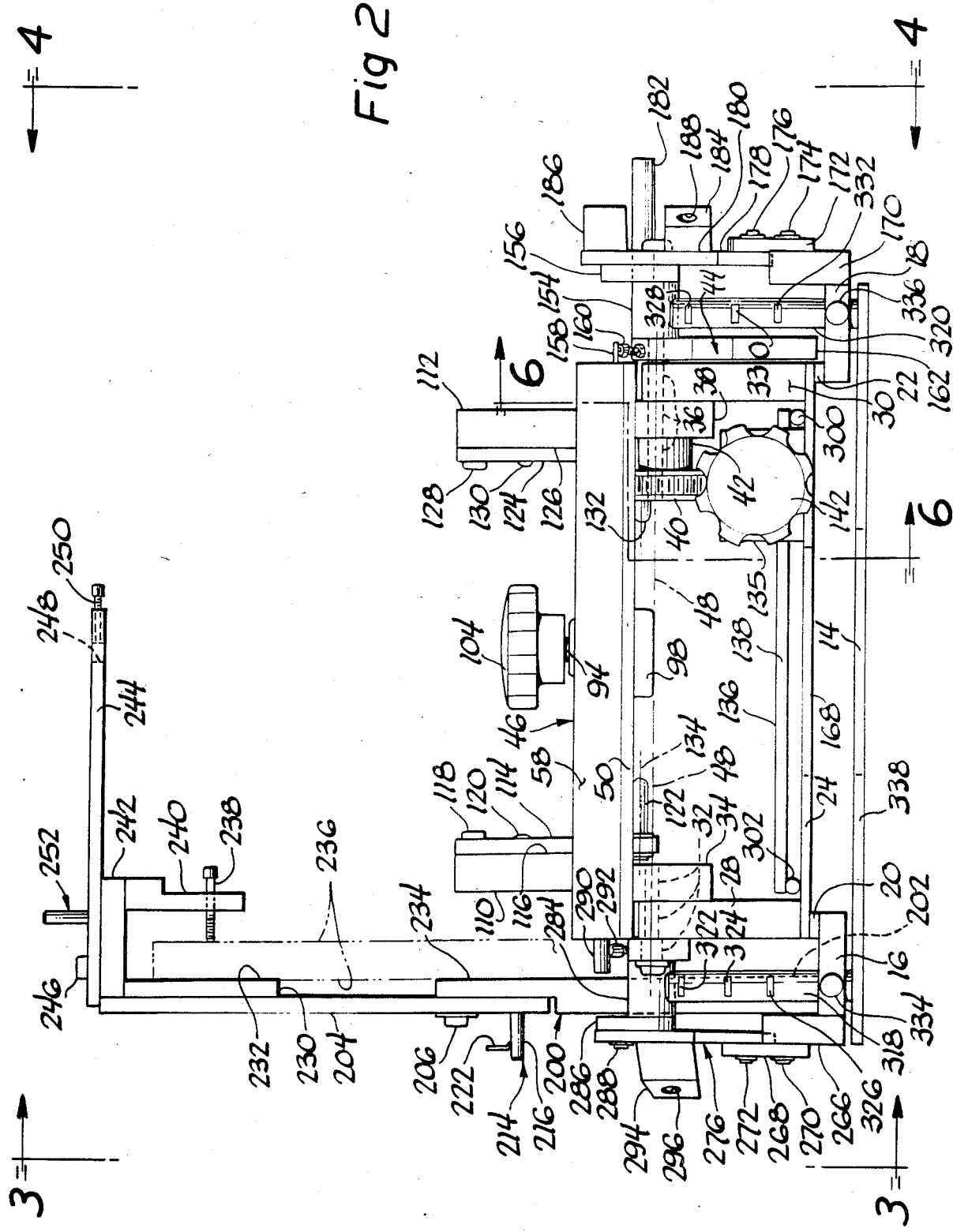

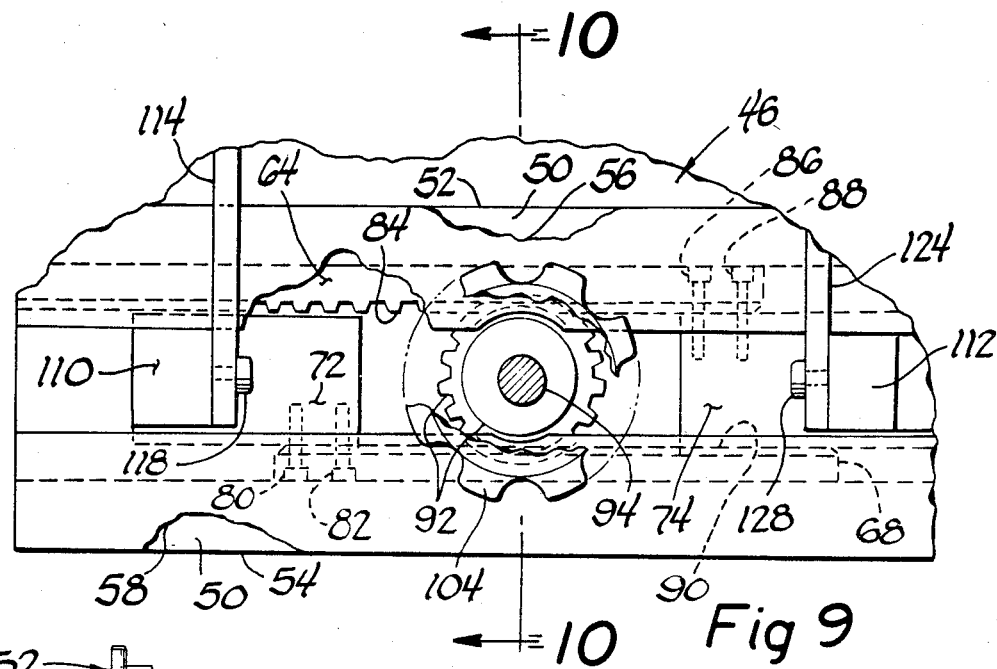
Fig 9
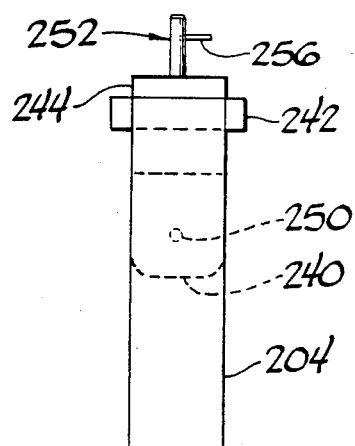
Fig 3
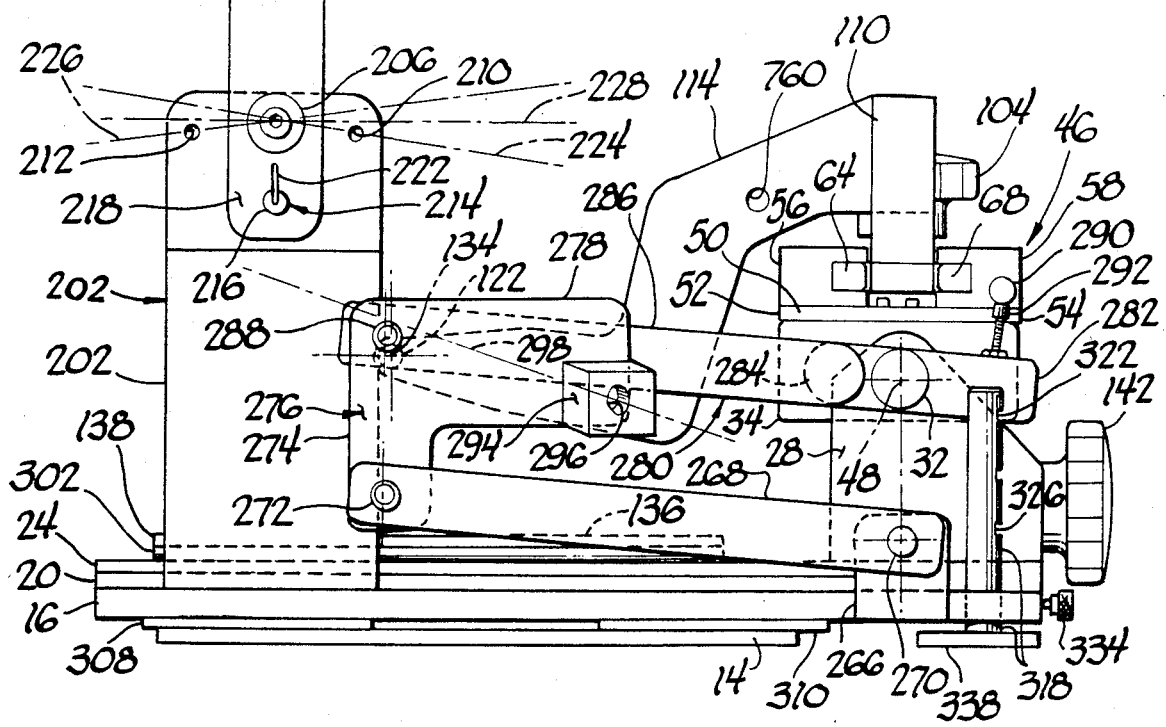

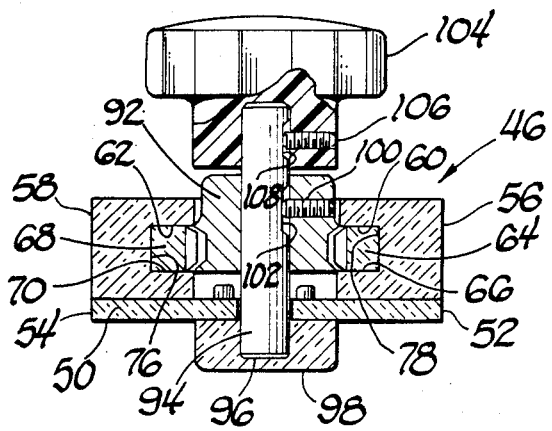
Fig 10
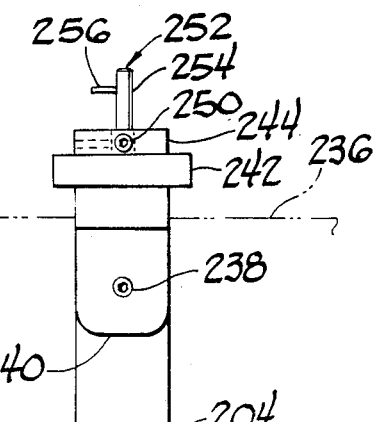
Fig 4
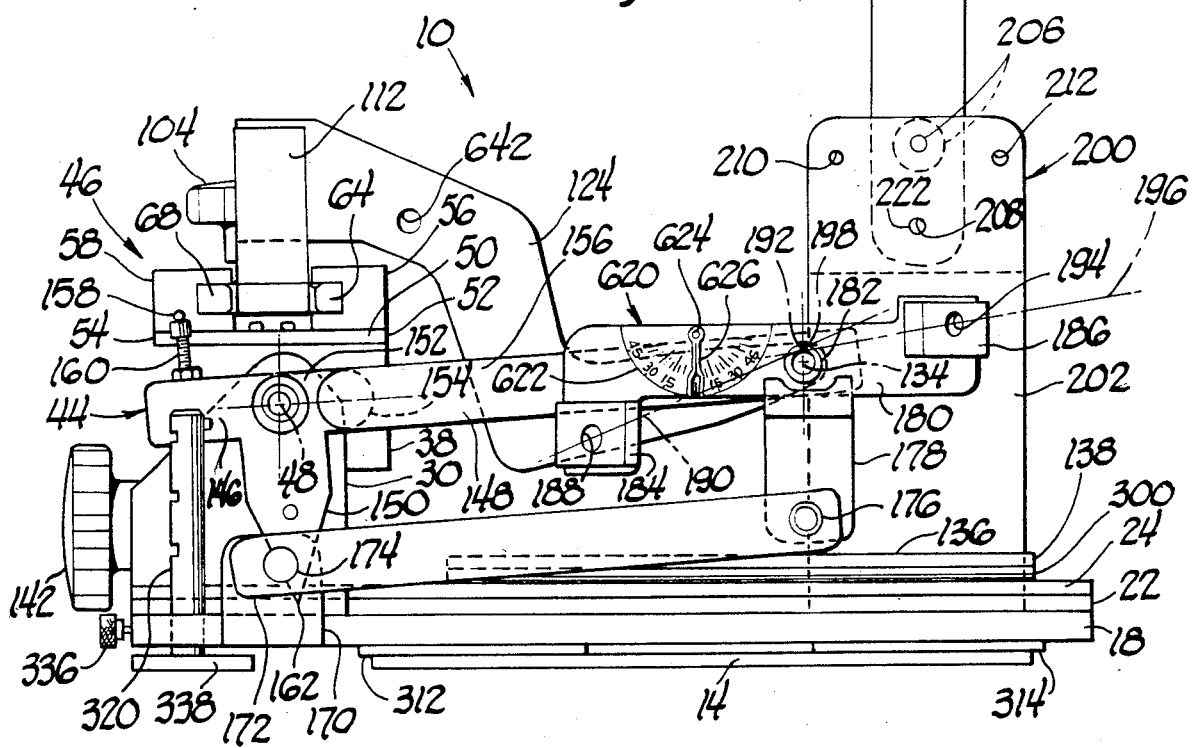

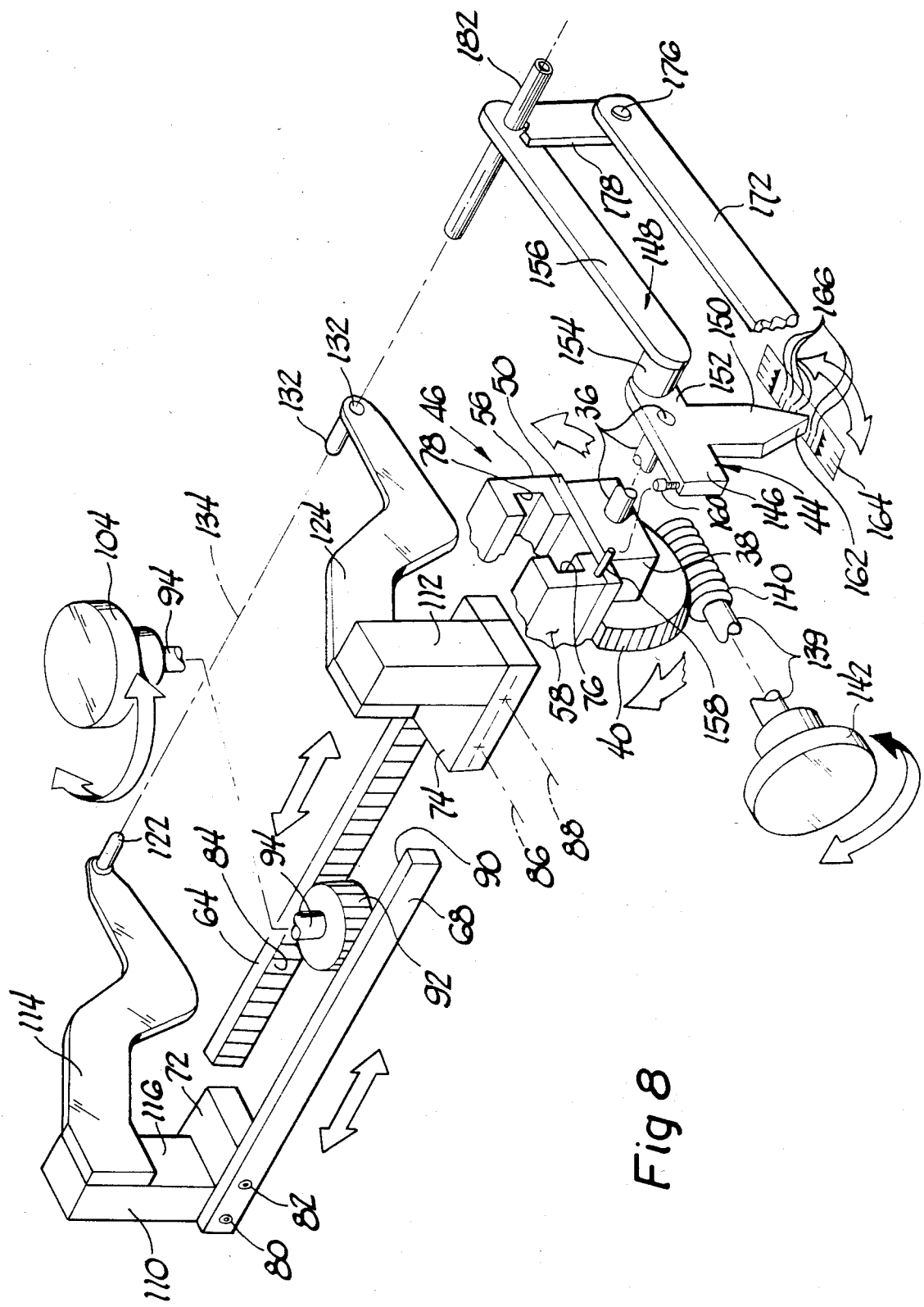

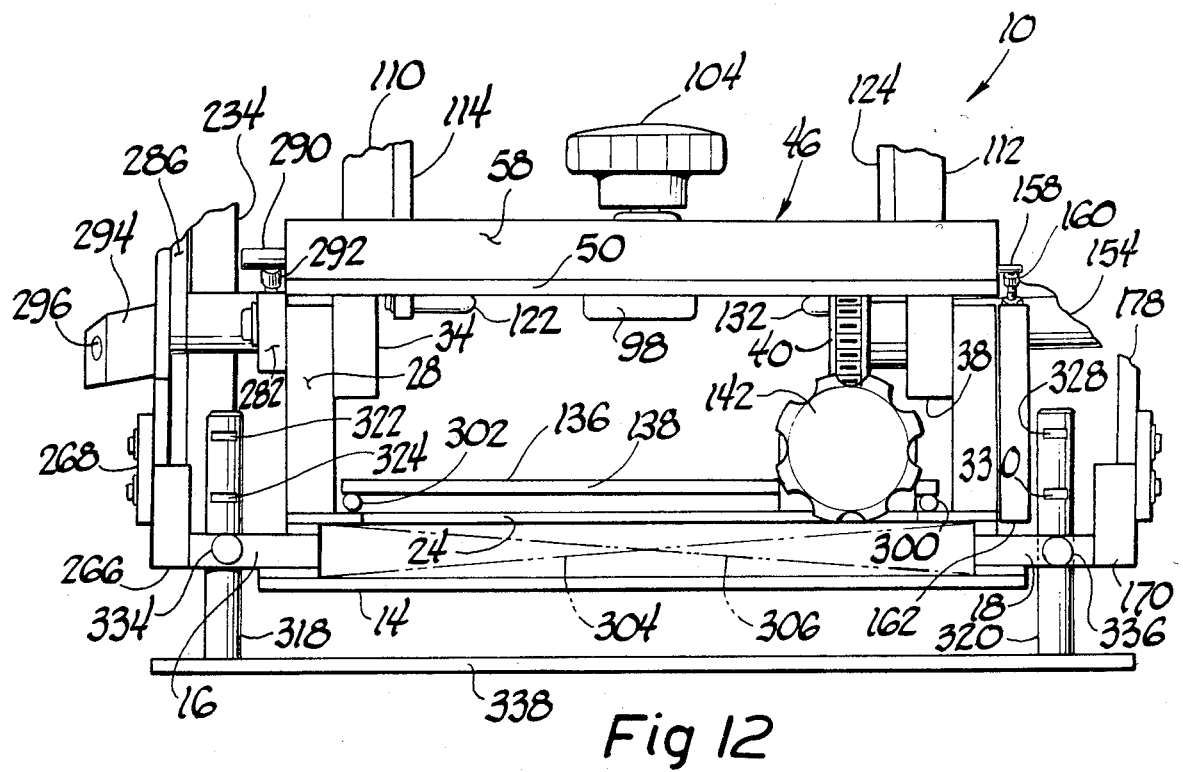

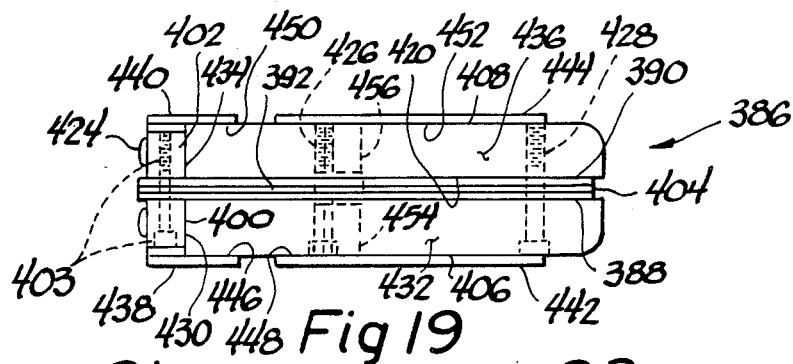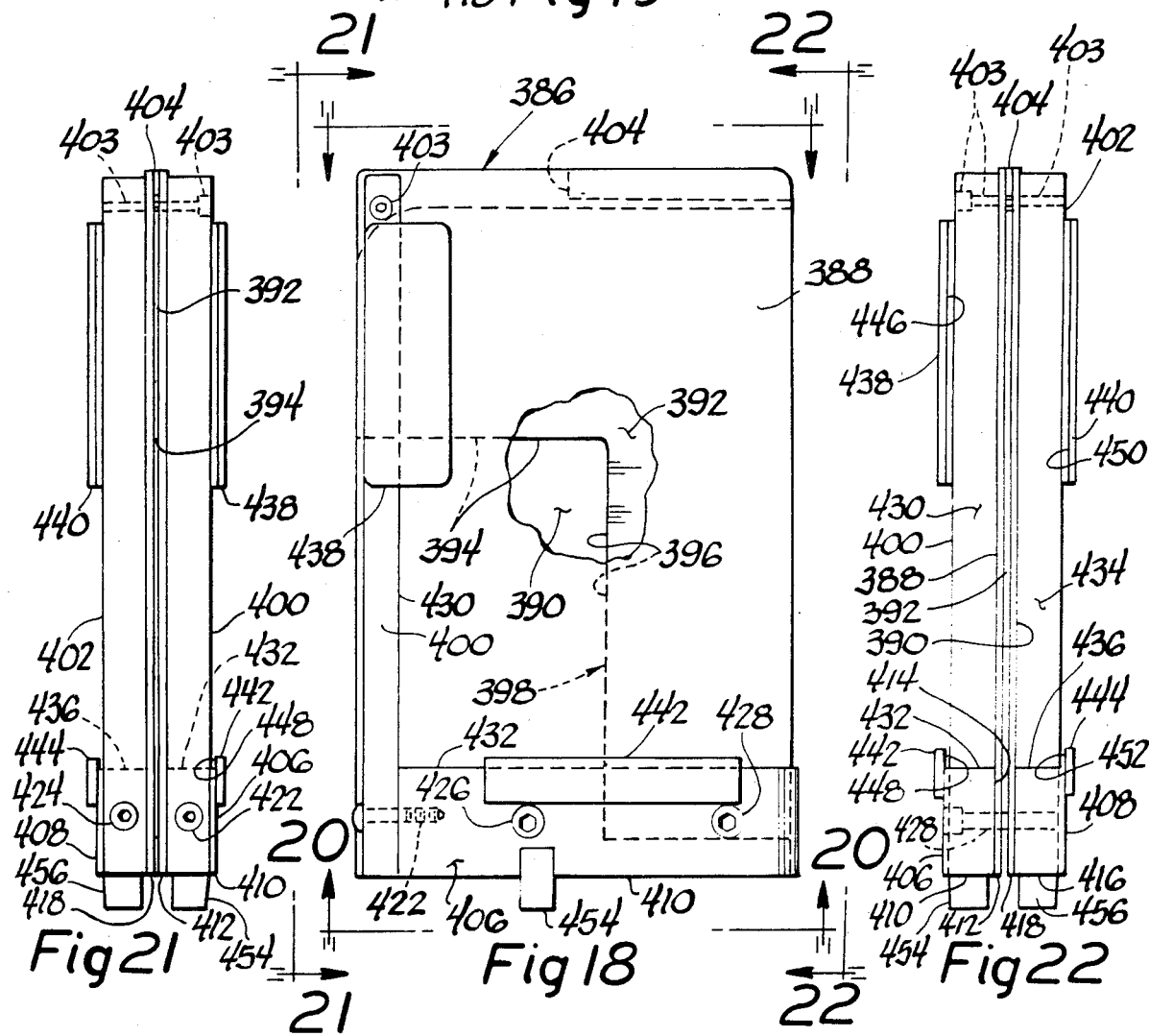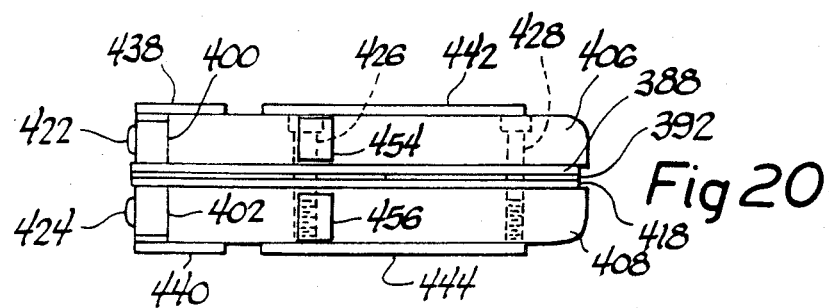

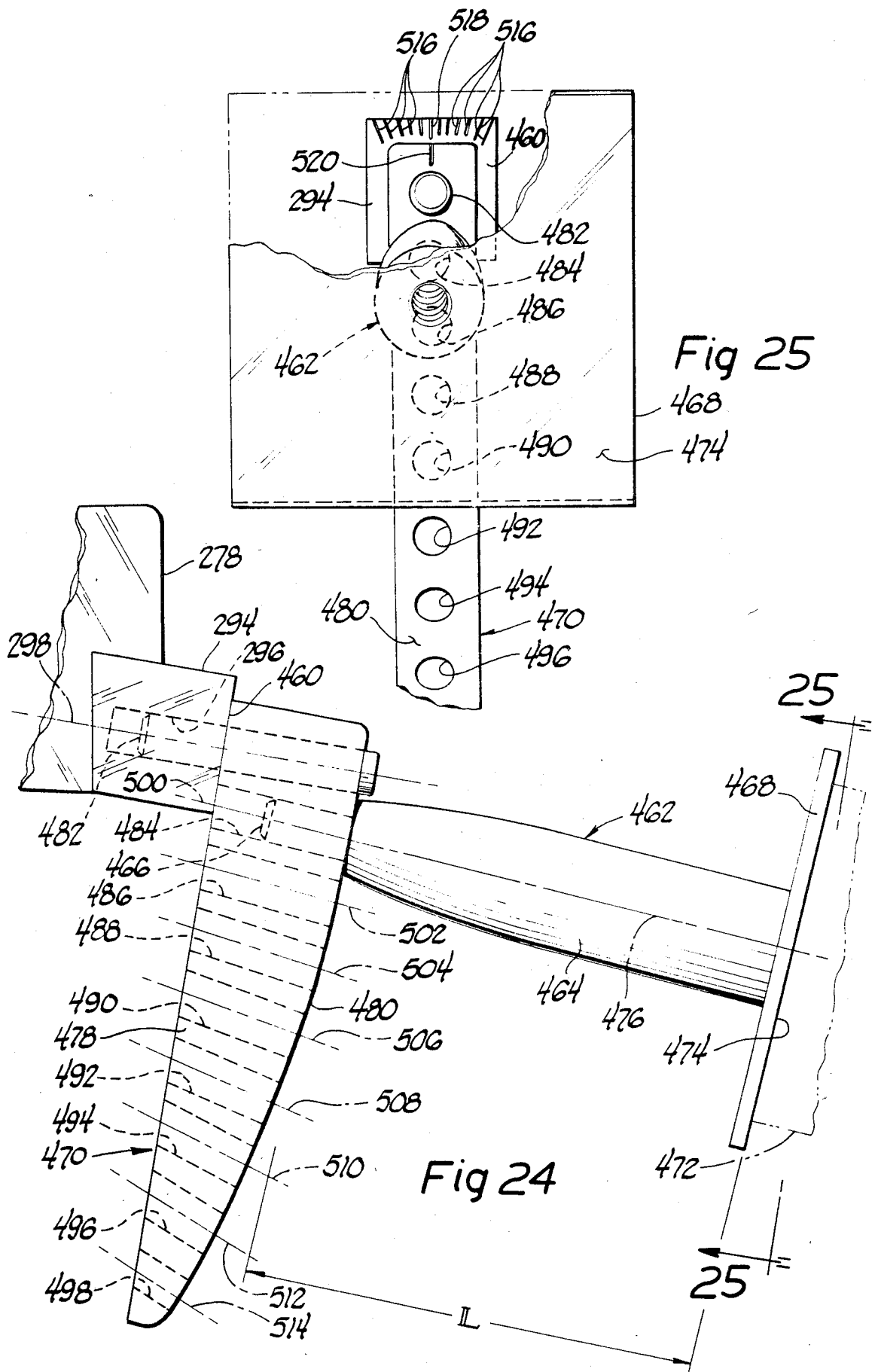

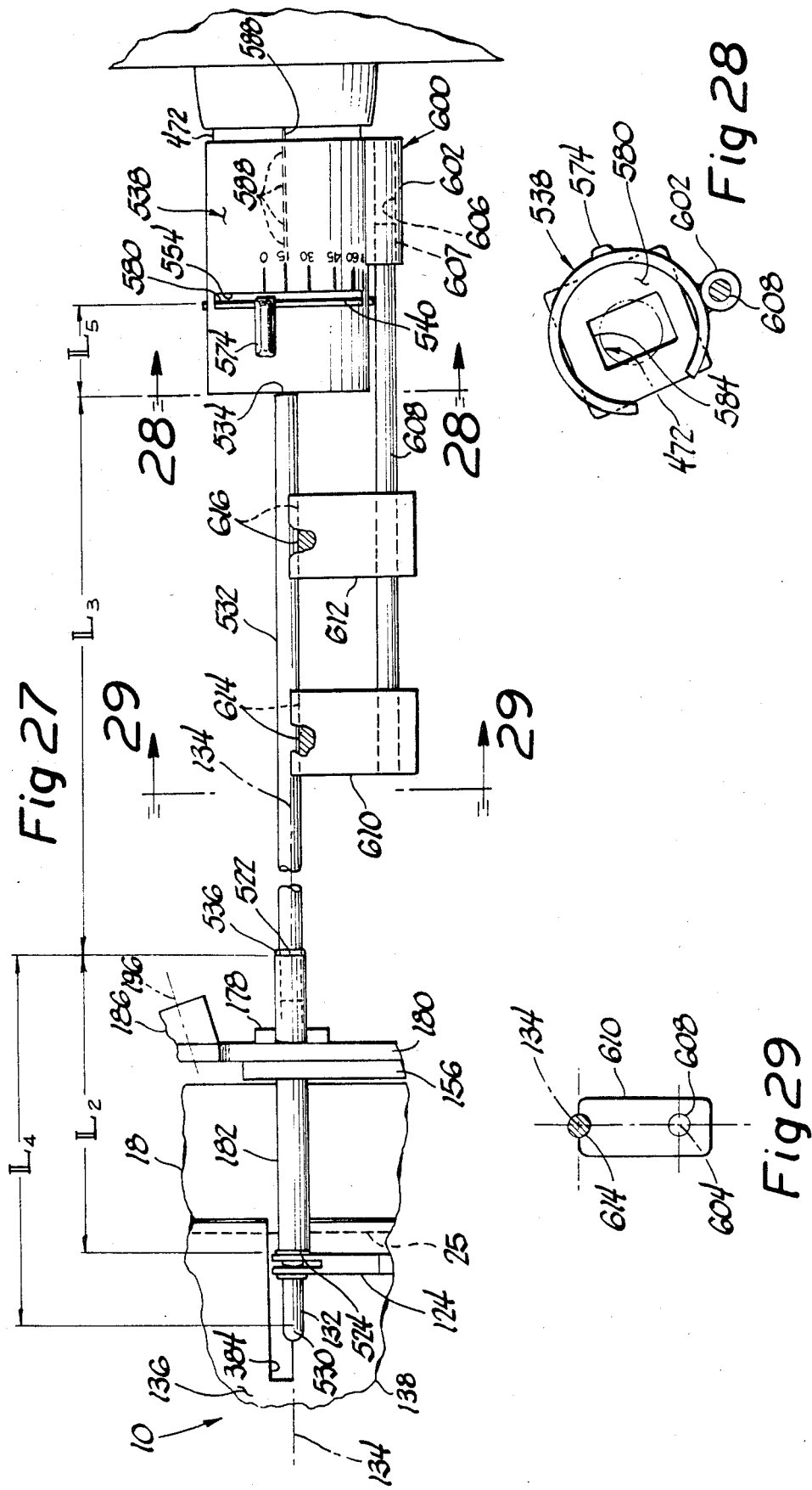

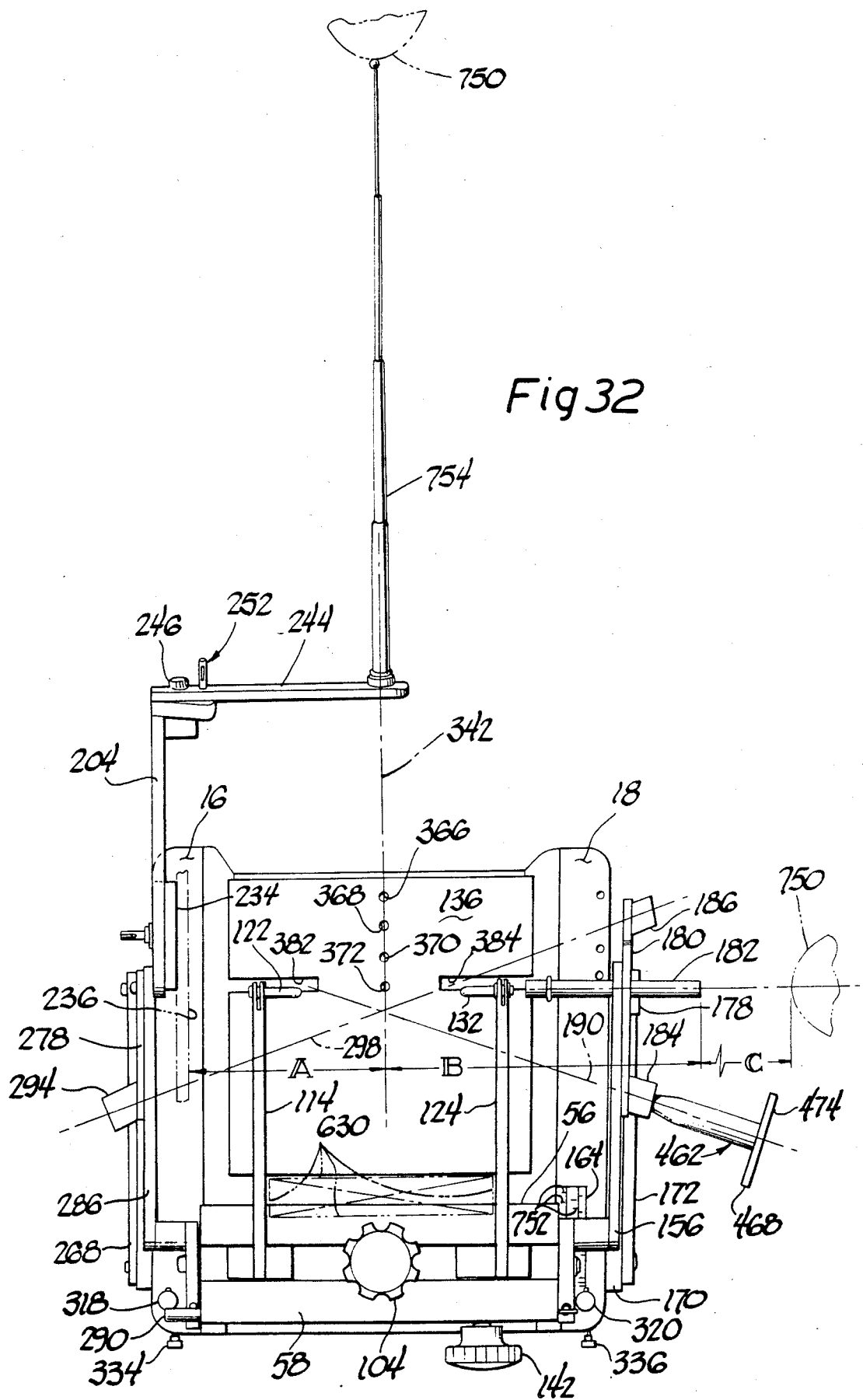

PORTABLE ROENTGENOGRAPHIC CEPHALOSTAT

RELATED APPLICATION

This application is a Continuation-in-Part of my application Ser. No. 453,949 filed on Dec. 28, 1982, for the invention entitled "PORTABLE ROENTGENOGRAPHIC CEPHALOSTAT".

FIELD OF THE INVENTION

This invention relates generally to cephalostatic apparatus and more particularly to such apparatus which is portable and enables the production of lateral and anterior-posterior cephalograms, as well as panoramic cephalograms, which are reproducible in terms of image magnification and degree of distortion.

BACKGROUND OF THE INVENTION

Heretofore many occassions have arisen where it was at least highly desirable to produce a cephalogram which would have the quality of reproducibility. For example, in the case of orthodontic procedures it is necessary to be able to produce cephalograms, spaced in time, to determine the degree of correction obtained by the prodecures employed. If the patient is an infant, or unable to stand or sit in order to be able to have such cephalograms take by conventional X-ray units designed for this purpose, the practitioner is, more often than not, unable to obtain the required cephalostatic cephalograms and must rely, in the main, upon the visual appearance of the patient or variably magnified and distorted cephalograms which, of course, may be deceiving of the actual situation.

In the instance of oral surgery, for example, if surgery were being performed on the jaw, it would be a distinct advantage for the surgeon to be able to determine the jaw configuration while the patient was still on the operating table. However, the prior art does not provide apparatus permitting such cephalograms to be taken of the patient while still on the operating table.

Further, it would also be of great benefit to the surgeon to be able to produce reproducible cephalograms in cases of cranial surgery, especially where the cranial bone is cut-off during the procedure, as, for example, in infants and young children, for the remediation of early cranial suture closure. That is, it is not uncommon in such procedures to insert bone markers on either side of a bone cut and to periodically thereafter take radiograms to see if the spacing between such bone markers, as well as naturally occurring land marks, has increased indicating displacement growth in the cranial system. It would be of material advantage to the surgeon if a pre-surgical and post-surgical cephalogram could be obtained showing the bone markers and cranial structures while the patient is still on the operating table. Also, such radiograms are difficult to obtain during the patient's convalescence due to patient age and need for sedation to obtain them. Again the prior art does not provide apparatus enabling such cephalograms to be taken of the patient while still on the operating table or in an X-ray department under sedation.

In all of such exemplary situations, among others, the purpose of the cephalogram is to be able to study and determine changes occurring over a significant span of time in, primarily, the bone structure of the patient. In order to be able to compare a series of such (spaced-in-time) cephalograms, and from that accurately determine what if any changes have occurred, and if occurred, the degree thereof, all variables must be eliminated in the process of obtaining each cephalogram. The prior art has failed to provide such apparatus with such capabilities which, further, could be employed in obtaining cephalograms of infants, invalids incapable of either standing or sitting, or of patients still on the operating table.

The invention as herein disclosed is directed generally to the solution of the above and other related and attendant problems of the prior art.

SUMMARY OF THE INVENTION

According to one aspect of the invention, a cephalostat comprises portable body means, first means for locating the back of a patient's head at a reference plane of elevation, second means for locating first unexposed film at a selected elevation below the back of the patient's head and at a preselected elevation below said plane of elevation, third means for locating second unexposed film to one side of the patient's head when the back of said patient's head is operatively located against said reference plane of elevation, fourth means for guidingly positioning said patient's head along said reference plane of elevation as to thereby place said patient's head as to have the mid-sagittal plane of said patient's head situated at a selected distance from said second unexposed film and for determining the elevation above the plane of said first film of the transporionic axis of said patient's auditory canals when the mid-sagittal plane of the patient's head is at said selected distance and fifth means for aiming a source of X-ray radiation at a selected angle with respect to said transporionic axis, said fifth means being effective for maintaining said selected angle regardless of the magnitude of elevation of said transporionic axis above said reference plane of elevation.

Various general and specific objects, advantages and aspects of the invention will become apparent when reference is made to the following detailed description considered in conjunction with the accompanying drawings.

BRIEF DESCRIPTION OF THE DRAWINGS

In the drawings, wherein for purposes of clarity certain details and/or elements may be omitted from one or more views:

FIG. 1 is a top plan view of a cephalostat employing teachings of the invention;

FIG. 2 is a front elevational view taken generally on the plane of line 2—2 of FIG. 1 and looking in the direction of the arrows;

FIG. 3 is an end elevational view taken generally on the plane of line 3—3 of either FIGS. 1 or 2 and looking in the direction of the arrows;

FIG. 4 is an end elevational view taken generally on the plane of line 4—4 of either FIGS. 1 or 2 and looking in the direction of the arrows;

FIG. 8 is a somewhat simplified perspective view of a portion of the operating mechanism shown in FIGS. 1, 2 and 3;

FIG. 9 is a view, relatively enlarged, of a fragmentary portion of the apparatus shown in FIGS. 1, 2 and 3;

FIG. 10 is a cross-sectional view taken generally on the plane of line 10—10 of FIG. 9 and looking in the direction of the arrows;

FIG. 11 is a view similar to a fragmentary portion of FIG. 4 but illustrating the apparatus of the invention adjusted as to be relatively inclined with respect to a supporting surface;

FIG. 12 is a view taken generally on the plane of line 12—12 of FIG. 11 and looking in the direction of the arrows;

FIG. 18 is a side elevational view of a film cassette holder or carrier which may be employed in the practice of the invention;

FIG. 19 is a view taken generally on the plane of line 19—19 of FIG. 18 and looking in the direction of the arrows;

FIG. 20 is a view taken generally on the plane of line 20—20 of FIG. 18 and looking in the direction of the arrows;

FIG. 21 is a view taken generally on the plane of line 21—21 of FIG. 18 and looking in the direction of the arrows;

FIG. 22 is a view taken generally on the plane of line 22—22 of FIG. 18 and looking in the direction of the arrows;

FIG. 24 is a relatively enlarged view of a fragmentary portion of certain of the elements shown in FIGS. 1, 2 and 3 along with related gauging and adjustment means operatively connected thereto;

FIG. 25 is a view taken generally on the plane of line 25—25 of FIG. 24 and looking in the direction of the arrows with portions of the structure being broken-away for purposes of clarity;

FIG. 27 is a top plan view of certain of the elements shown in FIGS. 1, 2 and 3 along with associated measuring, alignment and adjustment means which may be employed in practicing the invention along with a radiation or X-ray source;

FIG. 28 is a view taken generally on the plane of line 28—28 of FIG. 27 and looking in the direction of the arrows;

FIG. 29 is a view taken generally on the plane of line 29—29 of FIG. 27 and looking in the direction of the arrows;

FIG. 32 is a view similar to that of FIG. 1, in reduced scale and with considerably less detail, illustrating the apparatus of the invention as it may appear prior to, for example, the exposing of the unexposed film situated to the left of the patient's head and/or posterior to the top of the patient's head;

DETAILED DESCRIPTION OF THE PREFERRED EMBODIMENT OF THE INVENTION

Figure 5:
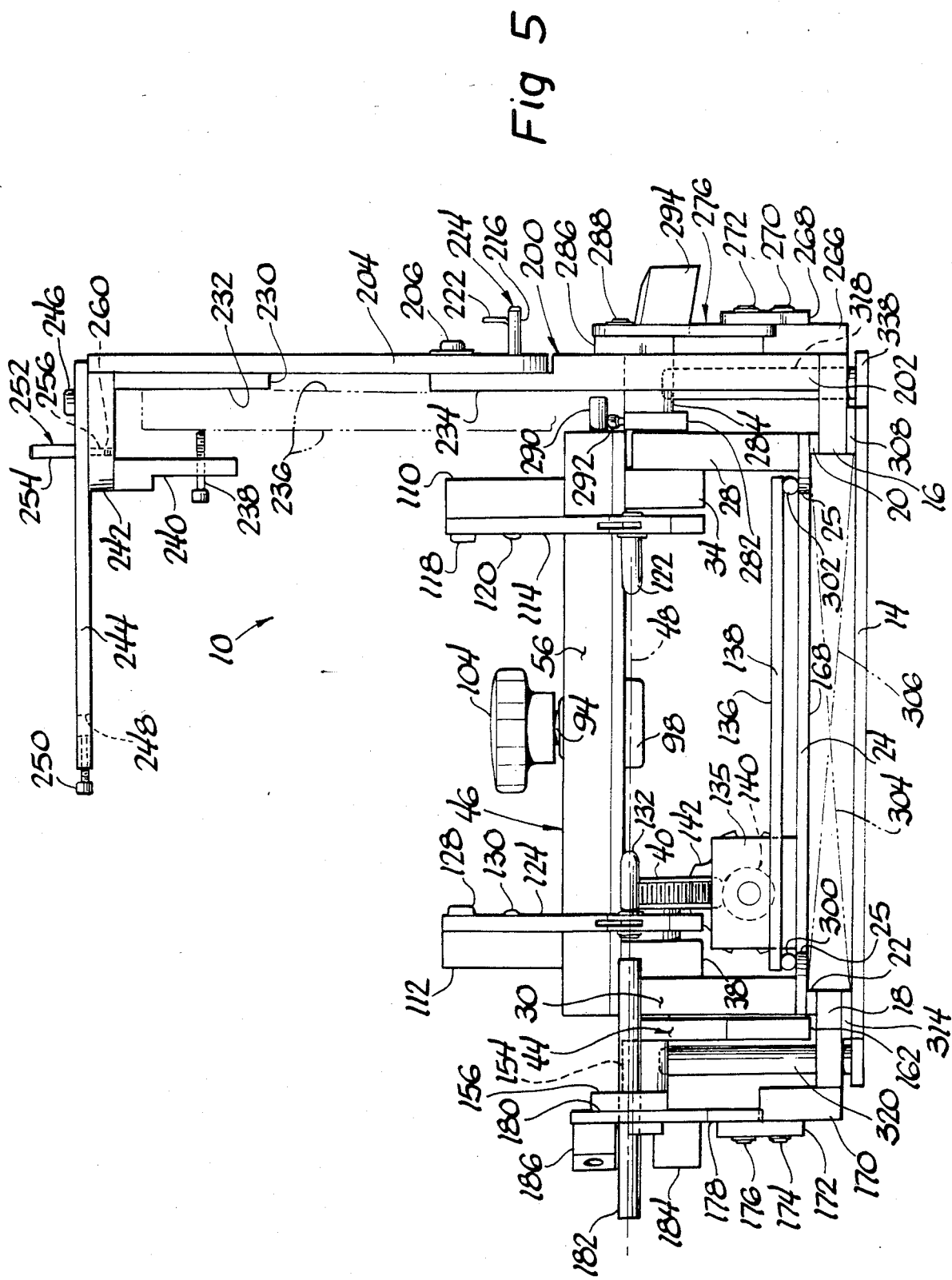
FIG. 5 is an elevational view taken generally on the plane of line 5—5 of FIG. 1 and looking in the direction of the arrows and being rotated 180°.

Referring now in greater detail to the drawings, and in particular to FIGS. 1, 2 and 3, the cephalostat 10 of the invention is illustrated as comprising frame or support means 12 which, in turn, preferably comprises a lower base plate 14 secured as by any suitable means such as, for example, screws or cement to a pair of oppositely disposed generally parallel and spaced frame members 16 and 18 which are situated as to be generally atop the base plate 14. A pair of spaced generally parallel spacer-like members 20 and 22 are, in turn, situated atop frame members 16 and 18 and, respectively suitably secured thereto, serve to support thereabove associated plate means 24. The plate means 24 may have formed therein an elongated slot 26 which can be used by a person to grip by hand for purposes of transporting the entire cephalostat 10.

The frame or support means 12 further comprises a pair of generally oppositely disposed trunnion-like or pivot support members 28 and 30 which may be formed of any suitable material. Such pivot support members 28 and 30 may be secured to the top of the laterally disposed plate means 24 in any suitable manner as by, for example, screws (not shown). As shown in, for example, FIG. 2, the support leg or member 28 carries a pivot or journal 32 which, in turn, extends through and supports an associated support block 34. Suitable means may be provided as to axially contain or retain the pivot means 32.

Referring in particular to FIGS. 2, 3 and 4, the support or leg member 30 is shown as pivotally carrying a shaft 36 which, as best seen in FIG. 2, extends to the left (as viewed in FIG. 2) of support member 30 and through an associated support block 38 and worm wheel means 40 along with integrally formed worm wheel hub means 42. As best seen in FIG. 2, in the preferred embodiment the shaft or pivot means 36 extends to the right (as viewed in FIG. 2) of support member 30 and into a lever or arm 44 which is suitably secured thereto for rotation therewith. The shaft 36 may also be secured to the worm wheel 40 and hub 42 as by any suitable keying or driving means so that an increment of rotation of the worm wheel means 40 results in a related increment of rotation of the shaft means 36. In the embodiment disclosed a pin, which may be generally parallel to shaft means 36, extends into both the worm wheel means 40 through hub means 42 and into support block 38 thereby fixedly connecting such for rotation in unison with each other.

In the preferred embodiment, as generally indicated in FIG. 2, the support or pivot block 38 is directly operatively connected to a platform assembly 46 through any suitable securing means so that rotation of gear 40 results in like rotation of platform assembly 46. Similarly, support block 34 is also fixedly secured by any suitable means, as by, for example, screws (not shown) to the inclinable platform assembly 46 for rotation therewith about the common centerline or axis 48 of rotation which is common to both pivot means 32 and 36.

Referring primarily to FIGS. 1, 2, 8, 9 and 10, the inclinable platform assembly 46 is illustrated as comprising a lower disposed generally rectilinear longitudinally extending base plate member 50 having opposed longitudinal edges 52 and 54 generally along which are situated generally C-shaped (or U-shaped) guides or ways 56 and 58, respectively. Formed integrally with and situated generally at the upper portion of the ways 56 and 58 are respective elongated keeper portions 60 and 62. The keeper portions 60 and 62, ways 56 and 58 and base plate 50 may all be secured to each other, to form a unitary structure, by any suitable means as, for example, screws.

A first gear rack 64 is slidably nested generally within way 56 as to be between upper keeper portion 60 and lower support or keeper portion 66 as to slidable longitudinally therealong. A second gear rack 68 is similarly slidably nested generally within way 58 as to be between upper keeper portion 62 and lower support or keeper portion 70 as to be slidable longitudinally therealong.

As illustrated in, for example, FIGS. 1, 3, 4, 8 and 9 a pair of sliding guide and support blocks 72 and 74 are provided. Slide block 72 sliding generally within recess 76 of way 58 and recess 78 of way 56 is suitably fixedly secured to gear rack 68, preferably by screws 80 and 82 as to thereby move in unison with gear rack 68. In the preferred arrangement, the thickness of slide block 72 may be substantially that of the width of the gear racks 64 and 68 and, further, the width of slide 72 is preferably such as to permit sliding motion as between the teeth 84 of gear rack 64 and the juxtaposed surface of slide block 72 whenever such experience relative motion, in, of course, the assembled state depicted as in, for example, FIGS. 1 or 4.

Similarly, slide block 74, sliding generally within recess 76 of way 58 and recess 78 of way 56 is suitably fixedly secured to gear rack 64, preferably by screws entering first through the rack 64 and then into slide body 74 with their respective centerlines depicted at 86 and 88 as to thereby move in unison with gear rack 64. In the preferred arrangement, the thickness of slide body 74 may be substantially that of the width of the gear racks 64 and 68 and, further, the width of slide 74 is such as to permit sliding motion as between the teeth 90 of gear rack 68 and the juxtaposed surface of slide block 74.

Accordingly, in view of the above, it can be seen that functionally gear rack 68 and slide body 72 are a unitary structure and that when gear rack 68 is made to move longitudinally, slide body 72 moves correspondingly in unison therewith. Further, the same applies to gear rack 64 and slide body 74; that is such comprise a functionally unitary structure and that when gear rack 64 is made to move longitudinally, slide body 74 moves correspondingly in unison therewith.

Referring in greater detail to FIGS. 1, 2, 8, 9 and 10, the manner in which such gear racks 64 and 68 are made to move is through a manually actuated gear 92. As possibly best seen in FIGS. 9 and 10, a gear 92 is situated generally between and in meshed engagement with the teeth 84 and 90 of respective gear racks so that rotation of the gear 92 in, for example, clockwise direction (as viewed in FIGS. 8 or 9) results in gear rack 64 moving to the right while gear rack 68 simultaneously moves to the left (as generally viewed in either FIGS. 8 or 9) while counter-clockwise rotation of gear 92 results in gear racks 64 and 68 simultaneously moving to left and right, respectively.

In the embodiment disclosed, a generally vertically extending gear shaft 94, having its lower axial end 96 rotatably and axially abuttingly received by an end thrust bearing block 98, suitably fixedly secured to the plate 50, is fixedly secured to the gear 92 as by a screw 100 threadably engaged with the hub portion of the gear 92 and abutting against a flatted portion 102 of shaft 94. A hand knob or handle 104 is similarly fixedly secured to shaft 94 for rotation in unison therewith as by cooperating screw 106 and flatted portion means 108. It should now be apparent that as knob or control 104 is rotated counter-clockwise, slide blocks or bodies 72 and 74 move linearly toward each other whereas when control means 104 is rotated clockwise, slide blocks or bodies 72 and 74 move linearly away from each other.

It should now be pointed out that the purpose of such slide bodies or blocks 72 and 74 is to support and carry respective support arm members 110 and 112, respectively.

In the construction of the preferred embodiment, such support arm members 110 and 112 are fixedly secured to the slide bodies 72 and 74, respectively, prior to the assembly of such slide bodies into and generally between ways 56 and 58. More particularly, referring to FIGS. 1, 2, 3, 8 and 9, the support member 110 is illustrated as being situated atop slide body 72 and secured thereto by any suitable means as to make such secured elements effectively of unitary structure. A generally cantilevered locating arm member 114 is preferably fixedly secured to the support arm 110, against surface 116, as by screws 118 and 120. The free end of locating arm 114 fixedly carries a generally cylindrical locating plug 122 of a preselected effective overall length.

Support arm 112, similarly, is situated atop slide body 74 and fixedly secured thereto by any suitable means as to make such secured elements effectively of unitary structure. The arm member 112 may be considered the mirror image of support arm 116. A generally cantilevered locating arm 124 is preferably fixedly secured to the support arm 112, as against surface 126, as by screws 128 and 130. The free end of locating arm 124 carries a locating member or plug 132 of preselected effective length which, preferably, is the same as that of locator member or plug 122.

The entire platform assembly 46 can be pivotally rotated about the aligned axes 48 of pivot means 32 and 36 and in so doing the height of the aligned centerlines 134 of locators 122 and 132 and, in so doing, the height of the aligned centerlines 134 of locators 122 and 132 is effectively raised or lowered relative to the reference plane 136 comprising the top surface of the head riser or locator member 138 upon which the back of the patient's head is set to rest. Of course, such upward and downward movement, in the embodiment disclosed, of the locators 122 and 132 is in an arcuate path with the radius of such arcuate path being the distance from the aligned axes 48 of pivot means 32 and 36 to the aligned axes 134 of locators 122 and 132.

Figure 6:
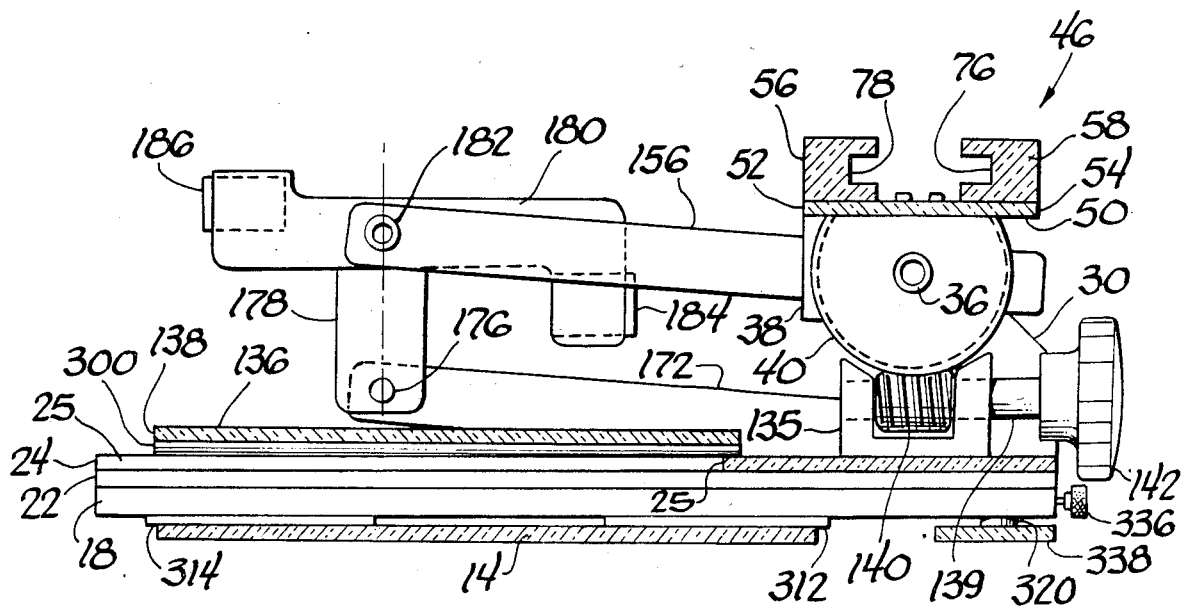
FIG. 6 is a cross-sectional view, taken generally on the plane of line 6—6 of FIG. 2 and looking in the direction of the arrows.
Figure 7:
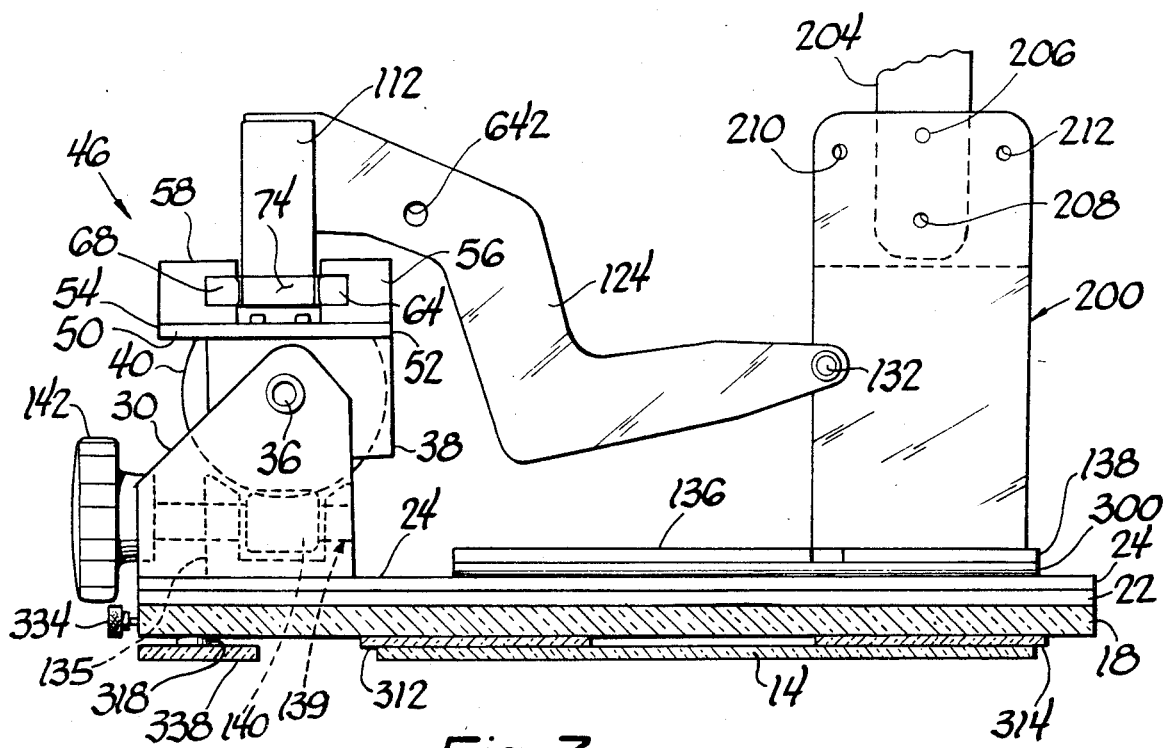
FIG. 7 is a view taken generally on the plane of line 7—7 of FIG. 1 and looking in the direction of the arrows.

Referring primarily to FIGS. 2, 6, 7 and 8, the manner and means by which the platform assembly 46 is controllably pivotally rotated about pivot means 32 and 36 is generally as follows. That is, as depicted in FIGS. 2 and 6, a worm shaft support block 135 is suitably fixedly secured as to the plate member 24 and, in turn, journals a shaft means 139 fixedly carrying a worm gear 140. One end of the shaft means 139 may be secured to a knob 142 as by, for example, a press-fit effectively locking the shaft means 139 to the knob 142.

As was previously described, block 38 is operatively secured to the platform base 24 and also to the worm gear 40 for unitary motion therewith. Accordingly, if the adjustment knob 142 is rotated, for example, clockwise the rotating worm shaft 139, engaged with worm gear 140, causes worm gear 140 to rotate in a corresponding clockwise direction. Since block 38 may be considered as driven by worm gear 140, and may be secured to platform base 50, such rotation of worm gear 140 causes a swingable rotation of the platform base 50 and, in fact, the entire platform assembly 46 in a clockwise direction (as viewed in, for example, FIG. 4 and 7 or 8). As a further consequence of such a swingable rotation, the free ends of locating arms 114 and 124 swing generally downwardly toward the plane 136.

If the adjustment knob 142 is rotated counterclockwise the resulting rotating worm shaft 139, engaged with worm gear 140, causes worm gear to rotate in a correspondingly counter-clockwise direction. Since block 38 may be considered as driven by worm gear 140 and may be secured to platform base 50, such rotation of worm gear 140 causes a swingable rotation of the platform base 50 and, in fact, the entire platform assembly 46. As a further consequence of such a swingable rotation of the platform assembly 46, the free ends of locating arm means 114 and 124 swing generally upwardly away from the plane 136.

As shown in, for example, FIGS. 1, 2, 4, 5 and 8, lever 44 is suitably operatively pivotally secured to shaft or pivot means 36 as to be pivotally rotatable, about axis 48, in unison with the platform assembly 46. As depicted in FIGS. 4 and 8, the lever 44 may be comprised of a first lever arm 146 and an oppositely disposed second lever arm 148 with a generally downwardly extending arm-like pointer or indicator 150. The arm 148, in turn, may be comprised of a relatively short arm section 152 with an off-set portion 154 to which is joined a relatively elongated arm portion 156. An abutment pin or means 158 is carried by the platform assembly 46 and is abutingly engaged by adjustment means, such as a threadably axially adjustable screw 160 carried by lever arm 146 of lever means 44.

The pointed end 162 of indicator means 150, as arm means 44 is rotatably swung about axis 48, passes rather closely to a related gauging means or seal 164 which may be carried as by the upper disposed surface of rail-like member 18. The gauging means or scale 164 carries a series of graduations or designations 166 thereon and such may be sequentially numbered, for example: "6", "7", "8", "9", "10", "11", "12", "13", "14", "15" and "16".

As previously described, rotation of knob 142 causes, as its ultimate purpose, the relative raising or lowering of the locators 122 and 132 (and the coaxial axes thereof). During such upward and downward movement of the locators 122 and 132, the abutment pin or means 158 causes a corresponding rotational movement of lever means 44 and pointer or indicator means 150. As the indicator means 150 and pointer end 162 are thusly caused to generally arcuately sweep above, and yet in juxtaposition to said gauging or scale means 164, the pointer end 162, when viewed in its general juxtaposed position to said gauging means 164 serves to indicate, to the operator, the actual elevation of the common axis of locators 122 and 132 above a lower reference surface or plane 168. For example, if through such rotation of knob 142, the common axis 134 of locators 122 and 132 is brought to a then selected position, and, let it be assumed, the pointer portion 162 of the indicator means 150 is juxtaposed to a numeral "11" on the scale or gauge means 164, then this, in the preferred embodiment, indicates to the operator that the actual elevation, of the common axis 134 of locators 122 and 132 is 11.0 cm. above the lower reference surface 168 of plate means 24. Similarly, if pointed portion 162 was seen to be juxtaposed to or aligned with a graduaction or designation identified as either said "6", "7", "8", "9", "10", "12", "13", "14", "15" or "16", such would indicate to the operator that the actual elevation or distance of the common axis 134, of locators 122 and 132, to the bottom or lower reference surface 168 of plate means 24 would be, respectively: 6.0 cm., 7.0 cm., 8.0 cm., 9.0 cm., 10.0 cm., 12.0 cm., 13.0 cm., 14.0 cm., 15.0 cm. or 16.0 cm.

Referring primarily to FIGS. 1, 2, 4, 5 and 8, a pivot support member 170, suitably fixedly secured as to rail-like member 18, pivotally supports a lever or linkage member 172 as by a pivot member 174. The other operative end of linkage member 172 is pivotally connected as by pivot means 176 to a depending like arm or linkage 178 which, in turn, is either integrally formed with or fixedly secured to a generally horizontally disposed member 180. A pivot member 182 extends through horizontal member 180 and arm portion 156 of lever 44 as to thereby pivotally interconnect such to each other. It should be pointed-out that in the preferred embodiment, generally, lever means 44, linkage 178, linkage or arm 172 and the structure comprised of support 170, base member 18 and support block 30 define a four-bar linkage means and more particularly a parallelogram wherein the distance between the axes of pivots 174 and 176 is substantially the same as the distance between the axis of pivot member 182 and axis 48 and, further, wherein the distance between the axes of pivots 182 and 176 is substantially the same as the distance between the axis of pivot 174 and axis 48. Also, in such preferred embodiment, when the cephalostat 10 is in its nominal horizontal position, as generally depicted in FIG. 4, the axes of pivots 182 and 176 are in vertical alignment as in axis 48 with respect to the axis of pivot 174.

As can be seen in, for example, each of FIGS. 1, 2 and 4, the generally horizontally disposed member 180 carries spaced body portions 184 and 186. As will be noted in for, example, FIGS. 1 and 4, body 184 is provided with a passage portion 188 which when viewed from the top (as in FIG. 1), is inclined, with respect to axis 134, in the order of, for example, 18° as to have the axis 190 of passage portion 188 appear to intersect (as viewed in FIG. 1) the axis 134, as at a point 192. Such apparent point of intersection is, preferably, at a distance of 2.0 inches to the left of the mid-sagittal plane as viewed in FIG. 1. Further, in the preferred embodiment, axis 190 is preferably at what could be considered a compound angle. That is, when viewed as in FIG. 1, axis 190 is inclined in the order of 18° from the transporionic axis 134; however, when viewed with respect to the reference surface 136, axis 190 is preferably inclined with respect thereto in the order of 8°. This, in turn, causes the axis 190 to pass above the transporionic axis 134 in a manner whereby the said apparent point 192 of intersection is actually vertically spaced, preferably, 1.0 cm. directly above the transporionic axis 134 as generally depicted in FIG. 4.

Still with reference to primarily FIGS. 1 and 4, body 186 is provided with a passage portion 194 which when viewed from the top (as in FIG. 1), is inclined, with respect to axis 134, in the order of, for example, 18° as to have the axis 196 of passage portion 194 appear to intersect (as viewed in FIG. 1) the axis 134, as at a point 198. Such apparent point of intersection is, preferably, at a distance of 2.0 inches to the right of the mid-sagittal plane as viewed in FIG. 1. Further, in the preferred embodiment, axis 196 is preferably at what could be considered a compound angle. That is, when viewed as in FIG. 1, axis 196 is inclined in the order of 18° from the transporionic axis 134; however, when viewed with respect to the reference surface 136, axis 196 is also inclined with respect thereto as, for example, in the order of 8°, as to cause the axis 196 to pass above transporionic axis 134 in a manner whereby the said apparent point 198 of intersection is actually vertically spaced, preferably, 1.0 cm. directly above the transporionic axis 134. Such point 198 would preferably then become, apparently coincident with point 192 when viewed in FIG. 4.

It should be made clear that because linkage 178 is either integrally formed with or fixedly secured to generally horizontal member 180 that when lever means 44 (comprising a portion of the described parallelogram) is pivotally rotated about axis 48, the attitude of neither the member 180, bodies 184, 186, passages 188, 194 nor axes 190 and 196 change but rather continue to maintain the established previously described relationship to the transporionic axis 134.

At the left end as viewed in FIGS. 1 and 2, a generally vertically upwardly extending plate or support means 200 is suitably operatively secured to the frame or base means 12. As also shown in FIGS. 4 and 5, the support means 200 is preferably comprised of a lower base-like plate portion 202 suitably secured as to member 16, at its lower end, and a second swingable plate or arm-like member 204 pivotally secured as by pivot means 206 to an upper portion of plate portion 202.

In the preferred embodiment, support member 202 is provided with a plurality of apertures or recesses 208, 210 and 212 with recess means 208 being situated as to have its axis parallel to and vertically spaced below the axis of pivot means 206. In the preferred embodiment, the upper arm or vertical member 204 is maintained in its vertical position by a locking or latching means 214. More particularly, the latching means may be comprised of a plunger housing or a body 216, fixedly secured to a lower arm portion 218 of member 204, which carries a spring-loaded plunger assembly which, in turn, is comprised of a plunger member 222, guidingly contained by said housing 216, spring means (not shown) urging such plunger member 222 into cooperative engagement with passage or aperture means 208. All that needs to be done in order to fold arm or support portion 204 is to pull the plunger member 222 to the left (as viewed in FIG. 2) thereby effectively withdrawing plunger member 222 from operative engagement with passage or aperture means 208 and then rotating support 204, depending upon choice, clockwise or counter-clockwise about pivot means 206.

As possibly best shown in FIGS. 3 and 4, the axes of passages or apertures 210 and 212, while preferably parallel to each other and to the pivotal axis of pivot means 206, are at a radial distance away from the pivotal axis of pivot means 206 equal to the radial distance that the axis of passage or aperture means 208 is spaced from the axis of pivot means 206. However, in such preferred embodiment, the respective axes of passage or aperture means 210 and 212 are also situated as to in respective planes 224 and 226, each containing the pivotal axis of pivot means 206 and respectively inclined, in opposite directions, in the order of 8° from a plane 228 which passes through the axis of pivot means 206 and is parallel to the reference surface 136.

Referring primarily to FIGS. 1, 2, 3, 4 and 5, the upper support member 204 carries a spacer or abutment member 230 the inner surface 232 of which in conjunction with the inner surface 234 of lower support member 202, provide a supporting plane against which an X-ray film cassette 236 can be placed and located. The lower end of the cassette 236, as viewed in FIG. 2, would be in vertical abutment as with the top surface of base member 16 and laterally (as also viewed in, FIG. 2) contained as between inner surface 234 of lower support 202 and the left side (as viewed in FIG. 2) of base member 20. The cassette 236 is preferably held at its upper end as by screw means 238 threadably engaged with and through a depending arm portion 240 suitably fixedly secured to a generally horizontally or laterally extending support arm 242 which, in turn, is suitably fixedly secured to upper support member 204.

The laterally extending support arm 242, in turn, pivotally supports a longer horizontally extending arm or lever 244 as by pivot means 246. The extended arm or lever 244 is provided with aperture or passage means 248 formed therein and a screw 250 threadably engaged as to be capable of, upon sufficient threadable rotation, extend into passage or aperture means 248. In the form of the embodiment disclosed, lateral support 242 is provided with a locking or latching means 252 which, similarly to means 214, may be comprised of a plunger housing or body 254, fixedly secured to extended lateral arm 244, which carries a spring-loaded plunger assembly which, in turn, is comprised of a plunger member 256, guidingly contained by said housing 254, and spring means (not shown) urging such plunger member 256 into cooperative engagement with a selected one of a plurality of apertures or passages 258, 260 and 262 formed in lateral support arm 242. As illustrated, the plunger member 256 is depicted as being operatively engaged with the medially situated passage or aperture means 260 thereby placing the plane or line interconnecting the axes of the pivot means 246 and aperture or passage means 248 perpendicular to the plane established by the inner surfaces, 232 and 234 as well as the film cassette 236. The alternate passage or aperture means 258 and 262 enable the disengagement of the plunger member 256 and passage or aperture 260 and the subsequent rotation of the extended arm 244 either clockwise or counterclockwise about the axis of pivot means 246 and the subsequent operative engagement of plunger 256 with either aperture means 262 or 258, respectively, if such should be desired for the particular medical procedure being performed.

Referring primarily to FIGS. 1, 2, 3 and 5, a pivot support member 266 suitably fixedly secured as to rail-like member 16, pivotally supports a lever or linkage member 268 as by a pivot member 270. The other operative end of linkage member 268 is pivotally connected as by pivot means 272 to a depending like arm portion 274 of a lever of linkage 276 which, in turn, has a second arm portion 278.

Situated generally above linkage 268 is a lever means 280 which may be comprised of a first arm portion 282 which, generally between its opposite ends, is pivotally secured as by pivot means 32 whereby such arm portion 282 is rotatable about the axis 48 of rotation of platform assembly 46. Generally opposite from the free swingable end of arm portion 282 a relatively short off-set portion 284 is fixedly carried and, in turn, fixedly secured to as to carry a relatively elongated arm portion 286. A pivot member 288 pivotally interconnects the other operative end of elongated arm portion 286 to the linkage or lever means 276.

An abutment pin or means 290 is carried by the platform assembly 46 and is abutingly engaged by adjustment means, such as a threadably axially adjustable screw 292 carried by the swingable end of arm portion 282 of lever means 280.

As shown, for example, in each of FIGS. 1, 2 and 3, arm 278 of linkage or lever means 276 carries a body means 294 suitably fixedly secured thereto.

It should be pointed-out that in the preferred embodiment, generally, lever means 268, linkage means 276, lever means 280 and the structure comprised of support 266, base member 16 and support block 28 define a four-bar linkage means and more particularly a parallelogram wherein the distance between the axes of pivots 272 and 288 is substantially equal to the distance between the axis of pivot member 270 and axis 48 and, further, wherein the distance between the axes of pivots 272 and 270 is substantially the same as the distance between the axis of pivot 288 and axis 48. Also, in such preferred embodiment, when the cephalostat 10 is in its nominal horizontal position, as generally depicted in FIG. 3, the axes of pivots 288 and 272 are in vertical alignment as in axis 48 with respect to the axis of pivot 270.

As will be noted in, for example, FIGS. 1 and 3, body 294 is provided with passage or recess means 296 which when viewed from the top (as in FIG. 1), is inclined, with respect to axis 134, in the order of, for example, 18° as to have the axis 298 of passage portion 296 appear to intersect (as viewed in FIG. 1) the axis 134, as at said point 198, previously described. The axis 298 is preferably at what could be considered a compound angle. That is, when viewed as in FIG. 1, axis 298 in inclined in the order of 18° from the transporionic axis 134; however, when viewed with respect to the reference surface 136, axis 298 is preferably inclined with respect thereto in the order of 8°. This, in turn, causes the axis 298 to pass above the transporionic axis 134 in a manner whereby the axis 298 passes through said apparent point 198 of intersection which, as previously described, is in the order of 1.0 cm. directly above the transporionic axis 134. Consequently, in the preferred embodiment, axis 298 is co-linear with axis 196 (FIG. 1). The preferred angles of axes 196, 298 and 190 recited herein and the resulting locations of the said apparent points of intersections 192 and 198 have been found to produce extremely good outlines of the patient's anatomical structure in the area of jaw joint.

It should be made clear that because linkage or arm means 276 is functionally solid, as between arm portions 274 and 278 that when lever means 280 (comprising a portion of the described parallelogram or four-bar linkage in FIG. 3) is pivotally rotated about the axis 48, the attitude of neither body 294 nor axis 298 changes but rather continue to maintain the established previously described relationship to the transporionic axis 134.

Referring primarily to FIGS. 1, 2, 3, 4, 5, 6 and 7, the generally horizontal plate 24 is preferably provided with a cut-out portion 25 as, for example, generally depicted in hidden line in FIG. 1 and as shown in elevation in FIG. 4. Plate 138, defining the reference surface 136, is, in turn, supported atop plate 24 as by spacer-like support members 300 and 302 which are respectively suitably fixedly secured to both plates 24 and 138 as by, for example, cementing. The actual spacer supports 300 and 302, or the functional equivalent thereof, are selected as to achieve a selected elevational distance as from, for example, reference surface 136 to the X-ray film to be exposed which, in FIG. 5 is intended to be represented by the crossed phantom lines 304 and 306 which would comprise an X-ray film cassette. In the preferred embodiment, the lateral distance as between side members 16 and 18 as well as the distance between base plate 14 and surface 168 of plate 24 are such as to slidably accommodate the X-ray film cassette 304–306.

As generally depicted in FIGS. 3, 4, 5, 6 and 7, if need be, suitable spacer means 308, 310, 312 and 314 may be provided as between the base plate 14 and the respective side members 16 and 18. Such base plate 14 and spacer means 308, 310, 312 and 314 may be fixedly secured to the rail or side member 16 and 18 by any suitable means as, for example, by screws or cement.

Referring primarily to FIGS. 11 and 12 along with FIGS. 1, 2, 3, 4 and 5, in some situations it may be desirable, even necessary, to have the cephalostat 10 inclined, as with respect to the table surface 316 upon which the patient reclines, in order to accommodate the patient or the particular circumstances attendant the particular medical procedure involved. In the preferred embodiment of the invention, this is accomplished as by a pair of axially slidable posts or adjustment members 318 and 320 respectively guidingly slidably received by side body members 16 and 18. When such adjustment members 318 and 320 are fully retracted, as generally depicted in, for example, FIGS. 2, 3, 4 and 5, the reference surface 136 would be effectively parallel to the table surface 316. Although other means of adjustment are, of course, possible in the preferred embodiment, as possibly best depicted in FIG. 2, the adjustment member 318 is provided with a series of notches or recesses 322, 324 and 326 while adjustment member 320 is similarly provided with a series of notches or recesses 328, 330 and 332. A first spring-loaded plunger-like assembly, having a plunger control knob 334, is carried by the side member 16 in a position as to have the line of action thereof effectively intersect the adjustment member 318. Similarly, a second spring-loaded plunger-like assembly, having a plunger control knob 336, is carried by the side member 18 in a position as to have the line of action thereof effectively intersect the adjustment member 320. (The details of such spring-loaded plunger-like assemblies are not shown since such are well known in the art.) A generally transversely extending foot plate or abutment means 338 is suitably fixedly secured to both adjustment members 318 and 320 as to be movable in unison therewith.

Whenever the cephalostat 10 is to be changed from its position as generally depicted in, for example, FIG. 4 to and inclined position as generally depicted in FIGS. 11 and 12, all that needs to be done is to pull-back (outwardly) on detent or plunger knobs 334 and 336 and move, or permit the movement of the foot or abutment means 338 downwardly the desired distance as may be represented, for example, when notches or recesses 326 and 332 are in respective alignment with the line of action of the plunger portions of which plunger knobs 334 and 336 comprise a portion. If that should be the desired inclination then at that time the spring-loaded plunger of control knob 334 is lockingly received by recess or slot means 326 and the spring-loaded plunger of knob 336 is lockingly received by recess means 332. This is, in simplified drawing typically depicted by a plunger portion 340 being received by slot or recess means 332 of adjustment member 320, in FIG. 11. The cephalostat 10, while thusly selectively inclined, nevertheless still contains the X-ray film cassette, as schematically designated by phantom lines 304 and 306 in FIG. 12, thereby still maintaining such cassette parallel to and at the preselected distance away from reference surface 136 of plate member 138.

Figure 14:
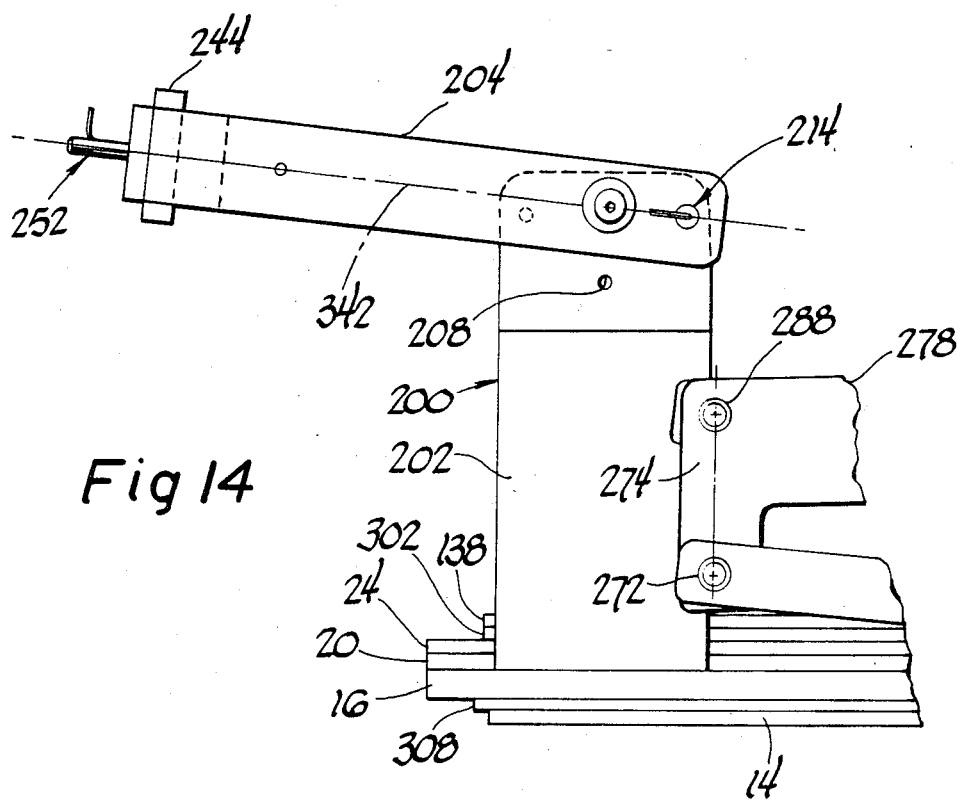
FIG. 14 is an elevational view of a fragmentary portion of the apparatus as shown in, for example, FIGS. 1, 2 and 3 with certain of the elements thereof being illustrated in an altered or selected adjusted position.
Figure 13:
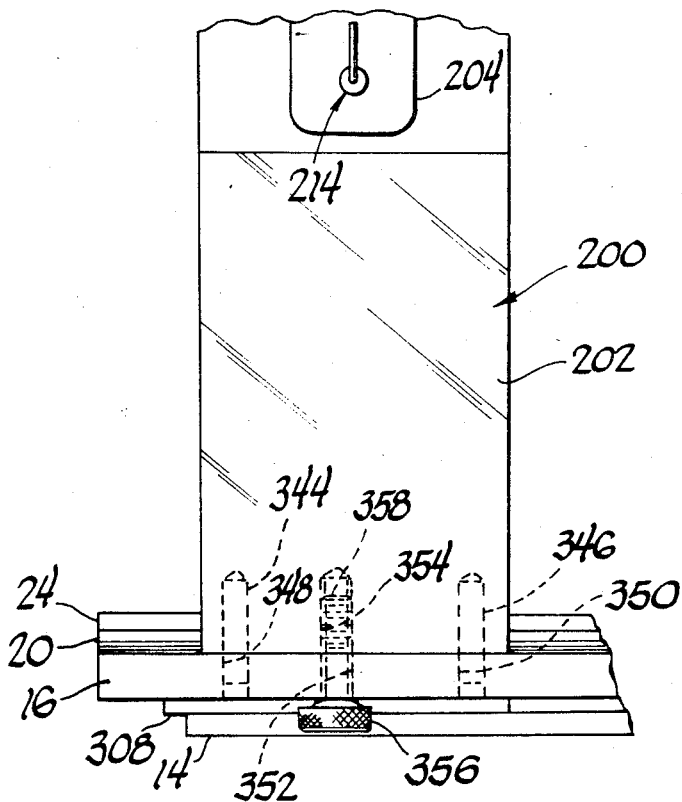
FIG. 13 is a relatively enlarged elevational view of a fragmentary portion of the apparatus as shown in, for example, FIGS. 1, 2 and 3.

As previously described, the upper arm 204 of the generally vertically extending support means 200 is pivotally rotatable to at least any of three selected positions one of which is depicted in FIGS. 2, 3, 4 and 5 and fragmentarily depicted as in FIGS. 6 and 13. A second selected position is depicted in FIG. 14 at which time the spring-loaded plunger means 214 is operatively engaged with aperture or passage means 210 (see FIG. 4) resulting in arm or lever 204 being so inclined as to have the axis, of aperture or passage 248 (see FIG. 1), represented by axis 342 in FIG. 14, being inclined at a preferred angle in the order of 8° with respect to the reference surface 136. Such an angle results in said axis 342 being effectively perpendicular to an X-ray film cassette if such cassette is placed generally between locating arms 114 and 124 with the lower portion of such cassette being abuttingly engaged by the relatively elevated edge 27 of reference plate 138 while the relatively upper portion of the cassette is abutingly engaged by or layed against way 56 thereby effectively tilting the X-ray film cassette at an angle in the order of 8° from the vertical and towards the carrier means 45. When viewed in FIG. 1, it can be seen that such axis 342 is also in the mid-sagittal plane.

In the preferred embodiment of the invention, the generally vertically extending support means 200 is so secured as to be detachable as from the left side of the cephalostat (as viewed in FIG. 1) and, in turn, secured to the right side. Referring primarily to FIGS. 1 and 13, in the preferred embodiment, this is accomplished as by having a pair of locating pins or dowels 344 and 346 press-fitted into body portion 202 of support means 200 with correspondingly situated close slip-fit passages or recesses 348 and 350 formed in side member 16 for closely but slidably respectively receiving therein pins 344 and 346. Further, side member 16 is provided with a clearance passage 352 which is aligned with an internally threaded passage 354 in body member 202. It will be noted that, in the preferred embodiment, the distance between the axis of dowel or locating pin 344 and the axis of clearance passage 352 and threaded passage 354 is considerably less than the distance between the axis of clearance passageway 352 and threaded passage 354 and the axis of locating pin 346. A thumb screw 356, or the like, extends through the clearance passage 352 as to have the threaded shank 358 thereof threadably engage threaded passage 354 as to thereby tighten and hold the support means 200 in assembled relationship against the side member 16.

The side rail or member 18, as depicted in FIG. 1 is somewhat similarly provided with apertures or passages 360 and 362 as well as a clearance passage 364. If the support means 200 were to be disassembled from the left side (member 16) and re-assembled to the right side (member 18) locating pin 346 would be closely but slidably received by passage 362, locating pin 344 would be closely but slidably received by passage 360 and clearance passage 364 would be in alignment with threaded passage 354 permitting screw 356 to again secure the support means 200, this time, to the right side of the cephalostat 10. The fact that the threaded passage is closer to locating pin 344 than to locating pin 346 along with the fact that clearance apertures or passages 352 and 364 are in like manner respectively closer to passages 348 and 362 permits the assembly of the support means 200 to the base or body means 12 in only one way thereby eliminating the possibility that in changing the location of such support means 200, such support means 200 would be re-assembled backwards. This, of course, comprises polarizing means.

The support plate 138 for the patient's head, and establishing the reference plane or surface 136, is preferably relatively thin of plexiglass or the like. The purpose of having the head support plate 138 relatively thin is to minimize, as much as practicable, the attenuation of the X-ray radiation as to the film 304–306 below the patient's head.

Figure 15:
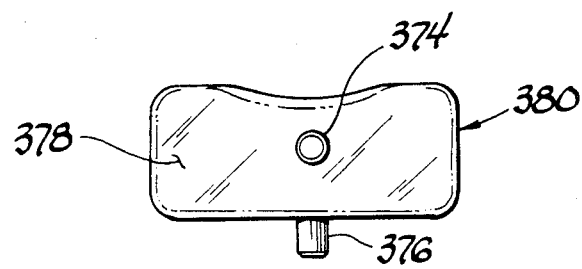
FIGS. 15, 16 and 17 illustrate a head-rest member, employable in practicing the invention and shown in FIGS. 16 and 17 as in combination with a fragmentary portion of the structure of FIGS. 1, 2 and 3.
Figure 16:
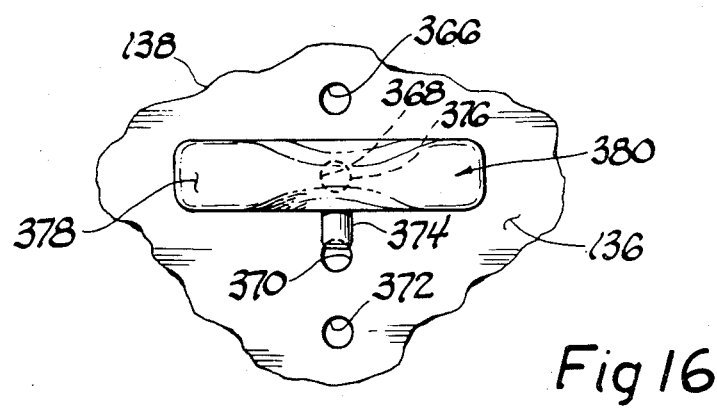
Figure 17:
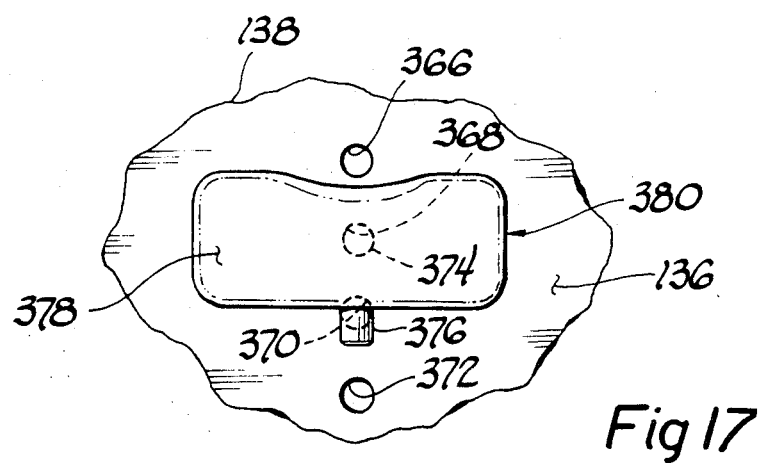

Further, in the preferred embodiment, a plurality of holes or passages 366, 368, 370 and 372 are preferably formed in plate 138 as generally depicted in FIG. 1. Such holes are intended to receive either of peg or rod-like portions 374 and 376 of the body 378 of a neck rest 380 as generally depicted in FIGS. 15, 16 and 17. The plurality of holes 366, 368, 370 and 372 in effect provide for adjustment due to the size of the patient's head while the choice of engaging either rod portion 374 or 376 will depend, primarily, on the age of the patient and the degree of curvature of the back of the neck at the base of the skull. Obviously, if rod portion 376 is engaged, the height of rest body 378 is comparatively higher than if the side-mounted rod portion 374 is engaged.

In addition to the cephalostat 10 being effective to employ X-ray film cassettes: (a) as at 236 held either at the left side by vertical support means 200 (shown in FIGS. 1 and 2) or at right side, held also by support means 200 when transferred to that side (b) the inclined X-ray film cassette, as previously described, cooperatively held by plate edge 27 and way 56; and (c) lower cassette 304–306 (FIGS. 5 and 12) the preferred embodiment of the invention contemplates the provision of additional means for, in turn, providing additional X-ray film cassette locations. Referring primarily to FIG. 1, the support plate 138 is provided with guide or keyway means 382 and 384 which, in effect, may be generally transversely extending slots formed in said support plate 138. Such recess or guide means 382 and 384 are primarily intended to guidingly retain holder means 386 for, in turn, holding an X-ray film cassette in an adjustably selected position or positions.

The preferred embodiment of such holder means 386 is best illustrated in FIGS. 18, 19, 20, 21 and 22. Referring in greater detail to FIGS. 18–22, the holder means 386 is illustrated as comprising a pair of relatively thin plexiglass walls 388, a portion of which is illustrated as being broken away, and 390 which are generally parallel to each other and which cooperatively contain a generally L-shaped plate of lead 392 therebetween. The edges 394 and 396 of the lead plate 392 cooperatively define a window-like opening 398.

A first generally vertically extending bar-like or abutment member 400 carried is generally along the left edge (as viewed in FIG. 18) of plexiglass wall 388 while a second generally vertically extending barlike or abutment member 402 is similarly carried along the left edge (as viewed in either FIGS. 18 or 19) of plexiglass wall 390. A screw 403 passes through the abutment member 400, near the top end thereof (as viewed in FIG. 18) and threadably engages with the generally oppositely disposed abutment member 402. A spacer 404, generally of the thickness of lead plate or shielding means 392 is situated between the walls 388 and 390, generally above lead plate 404, and suitably retained as by, for example, the cementing of such insert or spacer 404 to both walls 388 and 390. Accordingly, upon tightening of screw 403, and the fact that spacer 4 fixedly interconnects the upper right portions (as viewed in FIG. 18), the resulting squeezing of the abutment bars 400 and 402 against the respective juxtaposed walls 388 and 390 causes the walls 388 and 390 to retain, at least, the relatively upper portion of lead plate 392 in the depicted assembled relationship.

A first generally horizontally extending base or abutment member 406 is carried generally along the lower edge (as viewed in FIG. 18) of plexiglass wall 388 while a second generally horizontally extending base or abutment member 408 is similarly carried generally along the lower edge of plexiglass wall 390. As best seen in FIG. 18, the base member 406, at its left end, preferably, abuts against vertical bar or abutment member 400 and, at its lower edge or surface 410 may be in general alignment with the lower edge 412 of wall 388. The innermost surface 414 of base member 406 is shown as being in operative engagement with the outer planar surface of wall 388.

Similarly, base member 408, at its left end, preferably abuts against vertical bar or abutment 402 and, at its lower edge or surface 416 may be in general alignment with the lower edge 418 of wall 390. The innermost surface 420 of base member 408 is shown as being in operative engagement with the outer planar surface of wall 390.

Base member 406 may be fixedly secured to vertically extending bar or abutment 400 as by screw means 422 and, similarly, base member 408 may be fixedly secured to vertically extending bar or abutment 402 as by screw means 424. Further, generally transversely extending screws 426 and 428 extend through base member and, each, threadably engages the oppositely disposed base member 408. When such screws 426 and 428 are tightened, the base members 406 and 408 urge plexiglass watta 388 and 390 toward each other thereby firmly clamping the lower portion of lead plate 392 therebetween.

Vertical abutment member 400 and base member 406 have respective abutment surfaces 430 and 432 which, as will become more apparent, cooperate to define co-acting nesting or locating surfaces for an X-ray film cassette to be situated thereagainst and carried thereby. Similarly, vertical abutment member 402 and base member 408 have respective abutment surfaces 434 and 436 which, as also will become more apparent, cooperate to define co-acting nesting or locating surfaces for an X-ray film cassette to be situated thereagainst and carried thereby.

The vertically extending bars or abutment members 400 and 402 are respectively provided with fence-like portions 438 and 440, as near the respective tops thereof, which may be secured to the abutment members 400 and 402 by any suitable means as, for example, cementing. As depicted, each of the fence or retainer portions 438 and 440 extend to the right (as viewed in FIGS. 18 and 19) for some significant distance beyond the respective locating surfaces 430 and 434.

Similarly, the base abutment members 406 and 408 are respectively provided with fence-like portions 442 and 444 which may be secured to the base members 406and 408 by any suitable means as, for example, cementing. As depicted, each of the fence or retainer portions 442 and 444 extend upwardly (as viewed in FIGS. 18, 21 and 22) for some significant distance beyond the respective locating surfaces 432 and 436.

As generally illustrated, the inner surfaces 446 and 448 of retainers 438 and 442, respectively, are preferably coplanar as are respective inner surfaces 450 and 452, of retainers 440 and 444, coplanar to each other.

Further, base members 406 and 408 are respectively provided with key means or slidable guide means 454 and 456 which are aligned with each other and with such alignment being perpendicular to the planes as established by, for example: surfaces 446, 448; surfaces 450, 452 or the other respective surfaces of plates 388 and 390. The effective operating width of the guide means 454 and 456 is such as to be closely slidably received by slots 382 and 384 (FIG. 1). If desired, all of the elements comprising the carrier means 386, with the exception of lead plate 390 and the possible exception of the various screws, may be comprised of plexiglass.

With particular reference to FIGS. 1 and 18–22, a standard sized X-ray film cassette can be received against locating surfaces 430 and 432, between plate 388 and cooperating surfaces 446 and 448 or such X-ray film cassette can be received against locating surfaces 434, 436 and between locating surfaces 450 and 452. For purposes of example, let it be assumed that the back of the patient's head is against the reference surface 136 (FIG. 1) and that the locating arms 114, 124 have been moved inwardly somewhat as to properly place the ear canal locators 122 and 132 in engagement with the patient's ear canals. The X-ray film cassette carrier means 386 may then be placed into operative engagement with, for example, the slot 382 by slidably engaging the key means 454 and 456 therein. At that time, the lower surfaces 410 and 416 of respective base members 406 and 408 would be resting upon reference surface 136. When the carrier means 386 is thusly situated in slot 382, it (the carrier 386) is oriented as have the vertical abutment members 400 and 402 closer to or toward the pivotally mounted carrier assembly 46. In practice, the X-ray film cassette would be placed as to be nested or supported and located by surfaces 434 and 436 thereby placing the lead plate 404 effectively between itself and the source of the X-ray. The only area of the X-ray film thusly not shielded by the lead plate would be the cut-out window 398 which would define an area of approximately one-quarter of the exposable X-ray film area.

Figure 23:
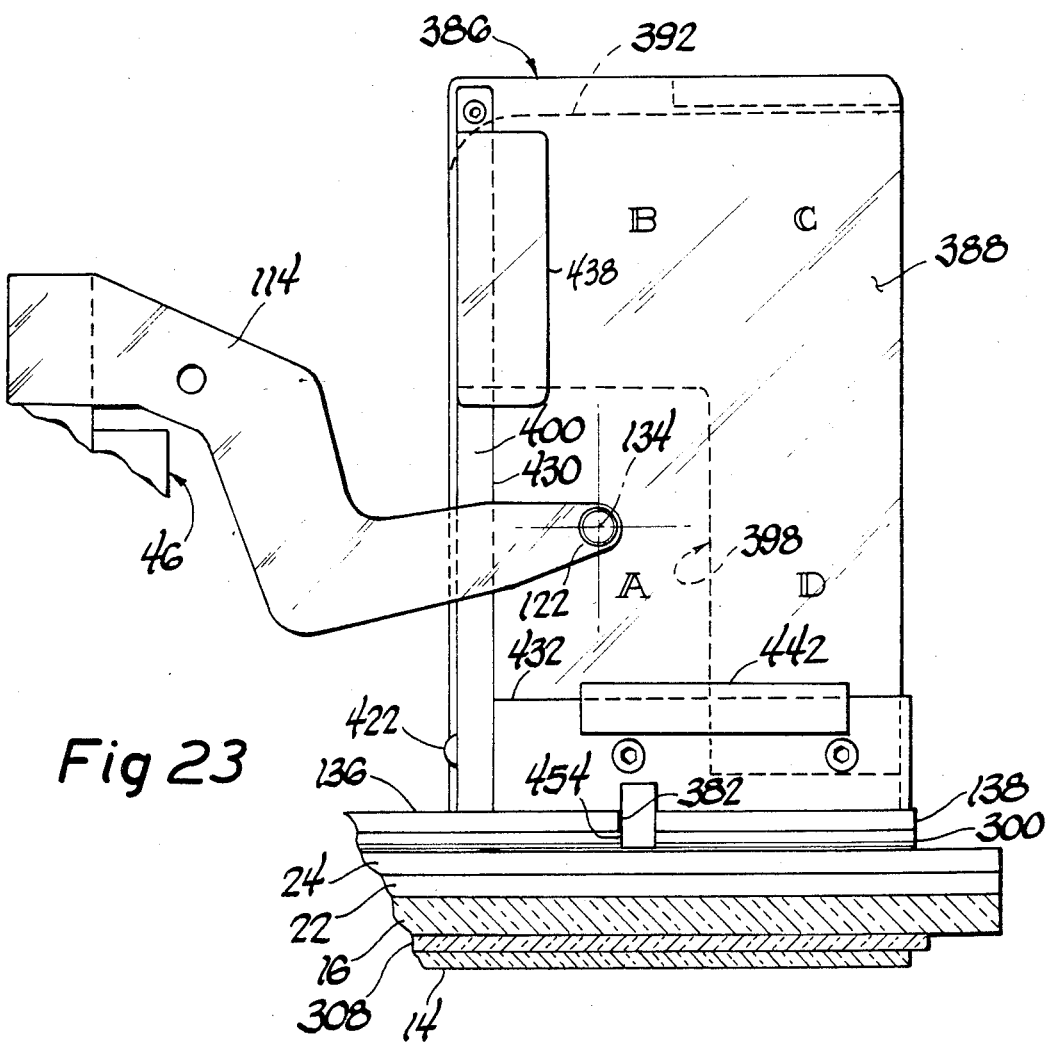
FIG. 23 is a fragmentary view, partly in cross-section of certain elements shown in FIGS. 1, 2 and 3 along with the film cassette holder of FIG. 18 in operational combination thereof.

In the preferred arrangement, the film cassette carrier means 386 would then be slid toward the patient's head until the juxtaposed side of abutment member 400 abutted against the locating arm 114 as generally depicted in FIG. 23. At that time the transporionic axis 134 would intersect the cut-out window 398 and correspondingly exposable film area at a location whereby, when X-rayed, the concerned anatomical structure would be within the confines of the area of window 398. This X-ray procedure would be referred to as a temporo-mandibular joint X-ray of the patient.

Further, for purposes of illustration, let it be assumed that the said X-ray film cassette is arbitrarily divided into four imaginary quarters (or quadrants) and that such are, further arbitrarily designated: A, B, C and D as generally depicted in and considered in a clockwise direction with respect to FIG. 23. Also, let it be assumed that the quarter-sector A has just become exposed but still located in juxtaposition to window 398. Now, if a second exposure of the same anatomical structure is desired, at the same angle or even at a different selected angle of exposure, the patient's head can remain positioned as it was and the X-ray film cassette removed from the carrier 386 and rotated so that the as yet unexposed quarter-sector area C is placed within the area defined by window 398 and then the said second exposure may be taken. At this time the previously designated film area A would have moved to the previously designated (as shown in FIG. 23) area C; the previously designated film area B would have moved to the previously designated (as shown in FIG. 23) area D; and the previously designated film area D would have moved to the previously designated (as shown in FIG. 23) area B. Consequently, with one X-ray film cassette it becomes possible, employing the carrier or holder 386 to obtain two exposures of the patient's left temporomandibular joint.

Now with the patient's head still being maintained in its original position, the holder or carrier 386 may be transferred to the right side of the patient's head, operatively engaged in slot or keyway 384 and brought into abutting engagement, this time, with locating arm 124. The same X-ray film cassette would then be transferred as to be now held and located by surfaces 430 and 432 to again place the lead shield 392 between it and the source of X-ray radiation. By so doing either the previously designated, and still unexposed area D or area B would become juxtaposed to the opening determined by window 398. A first exposure of the patient's right tempor-mandibular joint can then be taken thereby exposing the film area thusly defined by the area of window 398. If a second exposure is desired, whether at the same or different angle, the said X-ray film cassette is again rotated placing the diagonally opposite yet unexposed film area juxtaposed to the opening determined by window 398. A second exposure may then be made. From the preceding, it can be seen that by use of the holder or carrier means 386 it becomes possible to have four distinct exposures on one film thereby being able to quickly compare the images and saving the cost of film.

FIGS. 24 and 25 illustrate, in relatively enlarged scale means by which both the selected alignment and selected distance (in order to obtain the desired magnification) of the source of radiation can be established. FIGS. 24 and 25 are to be considered as typical and applicable to the body portions 294, 186 and 184, and their respective passages as illustrated in, for example, FIG. 1. Further, FIGS. 24 and 25 each illustrate what may be considered alternate arrangements. For purposes of orientation, let it be assumed that in FIG. 24 the view is taken as to be generally coplanar or parallel to the end surface 460 of body 294 of FIG. 1 and viewed in a direction toward, generally, the pivotal carrier means 46.

The primary gauging and alignment means 462 is illustrated as being comprised, for example, of a generally cylindrical body 464 with a cylindrical dowel or pin-like axial extension 466 at the left end (as viewed in FIG. 24) and a square abutment plate 468 carried as at its opposite end. Such primary gauging and alignment means 462 may, if intermediate member 470 were not to be employed, be directly connected with body means 294 as by the close, but slip-fit, reception of axial extension 466 into passage means 296 and having made the overall effective length or distance, L, to a preselected magnitude, the overall distance as to, for example, point 198 (FIGS. 1 or 4) would be known as well as would the distance from the point 198, and associated anatomical structure, to the related X-ray film to be exposed thereby assuring the desired degree of magnification once the X-ray machine cone 472, shown in phantom line, is placed squarely against abutment surface 474 of plate 468 and axially aligned with the axis 476 of gauging means 462 which, in the situation just described would be coincident with axis 298.

There are situations where the desired image to be obtained is one which would be at an angle different than that established solely by axis 298. In those situations, the intermediate member 470 may be employed. More specifically, the intermediate member 470 is preferably comprised of a body 478 which at its upper end (as viewed in FIG. 24) carries a locating pin or cylindrical extension 482 which is closely but slidably received within passage 296 of body 294. The body 478, which may have a slightly outer curvilinear surface 480, has formed therein (or therethrough) a plurality of passages or apertures 484, 486, 488, 490, 492, 494, 496 and 498 the respective axes of which are at, preferably, 3° increments with respect to the next adjacent one. Accordingly, if axis 298 is, for reference purposes, considered to be 0°, then axis 500 would be, relatively at 3°; axis 502 would be at 6°; axis 504 would be at 9°; axis 506 would be at 12°; axis 508 would be at 15°; axis 510 would be at 18°; axis 512 would be at 21° and axis 514 would be at 24°. The gauging and alignment means 462 may be placed into any selected passage 484-498 of intermediate member 470, as by means of coacting extension 466, and depending upon the passage selected the axis 476 of the gauging and alignment means 462 would assume the particular angular inclination of the axis of such selected passage. When the cone 472 of the X-ray machine would then be brought against the surface 474 of plate 468 and aligned with axis 476, it to would produce radiation at the same angle as the said axis of said selected passage. All of such axes 500-514 would pass through point 198.

In the preferred form, body 294 as on, for example, its surface 460 is provided with a plurality of angular graduations 516 (which, of course, may be numbered or otherwise identified) of which graduation or indicator 518 would serve as a zero-point. In cooperation therewith, intermediate member 470 may be provided with a reference line 520 or equivalent indicator means so that when, for example, indicator or reference means 520 is aligned with indicator 518 of indicator means 516, the intermediate member 470 would be in a vertical position. Such an arrangement would permit the rotation of the intermediate member to any particular selected angular position, about the axis 298 of passage 296 (or the axis of extension 482), as indicated, for example, by the then alignment of reference line 520 and a selected one of the angular indicators 516. Having thusly selected a particular angle for the subsequent X-ray exposure, the readings of the various settings can be recorded and, at some time in the future, if desired, the same angle of exposure can be re-established to make a comparison as to, for example, the ensuing healing process. Obviously, which ever particular angle is thusly selected, the X-ray machine cone 472 would be brought into juxtaposed alignment with the gauging and alignment means 462 as previously herein described.

As was already indicated, the arrangement of FIGS. 24 and 25 may be considered as being typical as with respect to, for example, body means 186 and 184 (FIGS. 1 and 4) and their respective axes 194 and 190. Further, with respect to such body means 196 and 184, the gauging and alignment means 462 (or the functional equivalent thereof) may be operatively connected directly to the body means 186 and/or 184, or through the intermediate member 470 (or the functional equivalent thereof).

Figure 26:
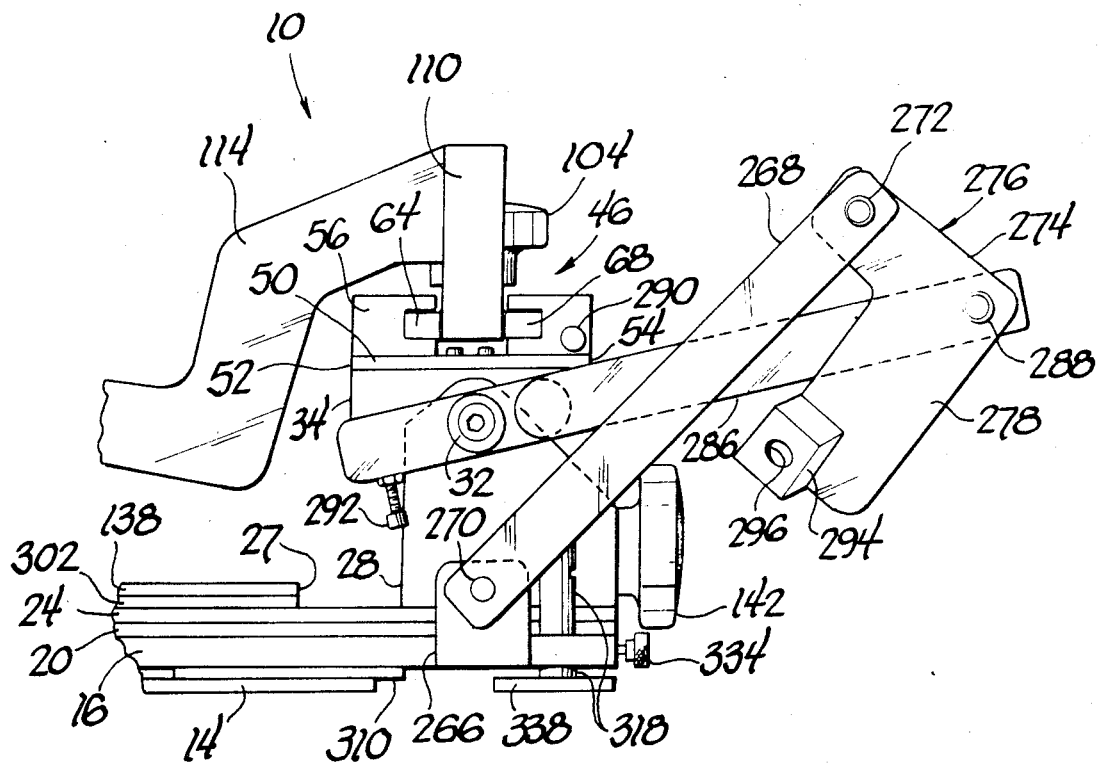
FIG. 26 is a view similar to a fragmentary portion of FIG. 3 but illustrating certain of the alignment or linkage means thereof in a position other than that depicted in FIG. 3.

For purposes of discussion, let it be assumed that the intermediate member 470 and the gauging and alignment means 462 have been assembled as shown in FIG. 24 and that the cone 472 of the X-ray source or machine has been properly abutted against surface 474 and properly aligned. At this time, in the preferred embodiment, the lever means or four-bar linkage means (as comprised of 286, 278, 288, 276, 272, 268, 32 and 270) is rotated out of the way as not to be between the source of the X-ray and the X-ray film. With reference to FIGS. 24, 3 and 26, this can be accomplished merely by rotating such four-bar linkage or parallelogram means generally counter-clockwise, as viewed in FIG. 3, until such linkage means attains a position as depicted in, for example, FIG. 26. Such rotation is accomplished, of course, without in any way having to move the cone 472 of the X-ray source from its previously established selected position.

Similarly, although not pictorially depicted, the four-bar linkage or parallelogram means of FIG. 4 (as comprised of, for example: 36, 148, 182, 178, 176, 172 and 174) may also be rotated out of the way as to be taken-out from between the aligned X-ray source and cooperating X-ray film, by a generally counter-clockwise rotation thereof as about pivot means 36 and 174 assuming a position which may be considered functionally equivalent to that as depicted in FIG. 26.

Referring primarily to FIGS. 1, 27, 28 and 29, the pivot means 182 not only serves as one of the pivot means comprising the parallelogram or four-bar linkage means (156, 178, 172) but also serves as an intermediate gauge or measuring means. More specifically, in the preferred embodiment the pivot means 182 comprises a cylindrically tubular member having, effectively, longitudinally extending substantially concentric inner and outer cylindrical surfaces. Further, such pivot means 182 is axially slidable to any selected position over its effective length. With reference to FIG. 1, it can be seen that end 522 of pivot means 182 is illustrated as being spaced a substantial distance to the right (as viewed in FIG. 1) of, for example, linkage or lever means 172 while the opposite end 524 is spaced from locating arm 124 and the right end 526 (as viewed in FIG. 1) of ear canal locator 132. The axial length of pivot or gauging means 182 may be of any suitable length; however, in the preferred embodiment once selected the said axial length is maintained and such may be in the order of, for example, 5.25 inches.

As generally depicted in FIG. 4, the axis of pivot means 182 is colinear or coincident with the transporionic axis 134 as determined by ear canal locators 122 and 132. Such a relationship is maintained as and when the pivot or gauging means 182 is axially moved relative to its associated structure.

For purposes of description, and referring primarily to FIGS. 1 and 27, let it be assumed that a patient's head is resting upon the reference surface 136 and that by manipulation of the control or adjustment knobs or handles 104 and 142, as previously described, the ear canal locators 122 and 132 are properly located and situated in the patient's respective ear canals. In this connection it should also be pointed-out that in the preferred embodiment distance-indicating indicia 528 are preferably provided as along the top surface of, for example, way 58 (FIG. 1) as to indicate the distance that the locating arms 114 and 124 (and therefore points 192 and 198) are apart from each other and half that distance would be to the mid-sagittal plane. In any event, let it be assumed that when such ear canal locators are thusly properly situated, the fragmentary portion of cephalostat 10 in FIG. 27 illustrates the then determined position of ear canal locator 132. For all practical purposes, a particular axial point 530 on the ear locator 132 may be established as being, on the average, in the plane which generally contains the tempor-mandibular joint so that, as a consequence, a dimensional constant is established as between such point 530 and the end 524 when as depicted in FIG. 27. (The same may, of course be determined and established on the left ear canal locator 122.) This then results in a dimensional constant of $L_4$. The distance from the X-ray film to be exposed as, for example, at 236 to the point 530 can be measured or determined as by, for example, graduations or indicia 528. Knowing such distances, it then becomes a simple matter to calculate the length or distance $L_3$ to the source of radiation in order to obtain the desired degree of magnification in the film exposure. For ease and clarity of description a measuring or gauge rod 532 is depicted as being of fixed axial length equal to the desired dimension $L_3$ from the end 522 of member 182 to the right or free end 534 of rod 532 The member 532 may be provided with an annular of flange-like axial abutment portion 536 which serves to abut against end 522 of member 182 while permitting a portion of rod means 532 to be closely slidably received within the tubular member 182. In practice, the measuring or gauging means 532 may be of a type which is selectively axially extendable as to thereby, with one such measuring rod being able to extend to any desired length, $L_3$, and subsequently bring the cone 472 of the radiation source, effectively, to the extended end and in alignment therewith.

In the embodiment depicted in FIG. 27, the cone 472 of the radiation source is provided with a sleeve-like adapter 538 which, selectively, may or may not be used, as illustrated, in combination with the cone 472 of the radiation source. When such a combination is employed, the free end of the cone 472 operatively abuts as against a plate 540 so that the distance, $L_5$, from the abutted free end of cone 472 to the extended free end of adapter means 538 becomes a fixed or constant dimension taken into account in determining the value or magnitude of distance $L_3$.

Figure 30:
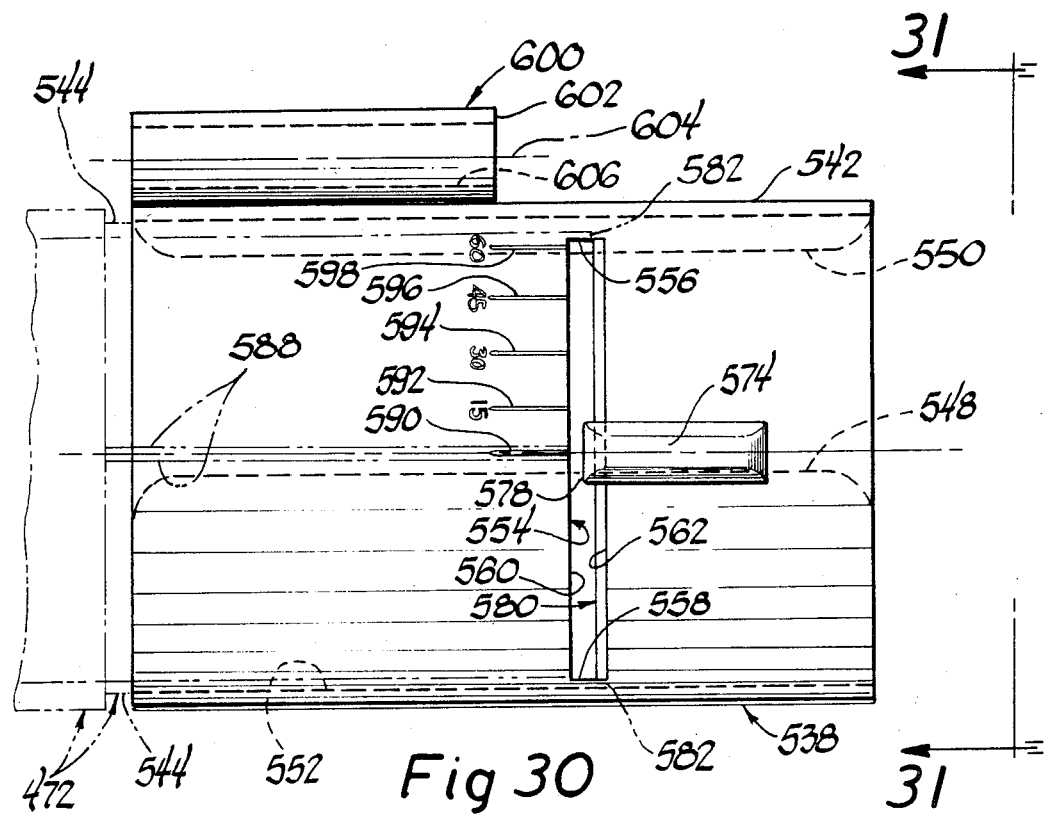
FIG. 30 is a relatively enlarged generally top plan view of one of the elements shown in FIG. 27.
Figure 31:
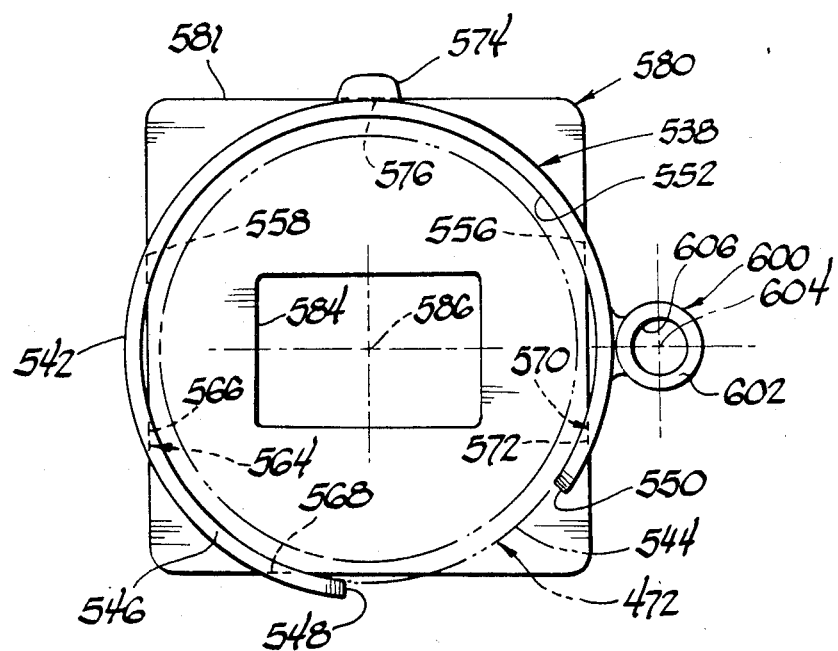
FIG. 31 is a view taken generally on the plane of line 31—31 of FIG. 30 and looking in the direction of the arrows.

Referring also to FIGS. 30 and 31, the adapter means 538 is illustrated as comprising a generally sleeve-like or tubular-like main body portion 542 which may be formed as from tubular stock of an internal diameter slightly less than the outer diameter 544 of radiation source cone 472. The wall 546 of such tubular stock may then be cut as to remove a portion thereof and define resulting axially extending edges 548 and 550. If, as in the preferred embodiment the said tubular stock has some resiliency such as, for example, plexiglass, the edges 548 and 550 can be resiliently deflected outwardly or away from each other thereby enabling the outer cylindrical diameter 544 of the cone 472 to be received within inner generally cylindrical surface 552 of the adapter body 542 as generally depicted in FIGS. 30 and 31. Once the thusly spread edges 548 and 550 are released, the inherent resilience of the material will cause the adapter body 542 to frictionally engage and retain the adapter means 538 on the tubular cylindrical surface 544 of cone 472.

Referring to FIG. 30 which, for purposes of reference, may be considered the top of the adapter means 538, a generally transversely extending slot 554, having end surfaces 556, 558 and transverse side surfaces 560, 562, is formed through the top of adapter body 542. A second slot 564, comprised of end surfaces 566 and 568 and side walls or surfaces which are respectively coplanar with surfaces 560 and 562, is formed in the generally lower left portion (as viewed in FIG. 31) of the adapter body 542. End surface 566 may be effectively coplanar with end surface 558 and generally perpendicular to end surface 568. A third open-ended slot 570, comprised of an end surface 572 and side walls or surfaces which are respectively coplanar with surfaces 560 and 562, is formed in the lower right portion (as viewed in FIG. 31) of the adapter body 542. End surface 572 may be effectively coplanar with end surface 556.

An abutment portion 574 is carried atop the adapter body 542 and has its left end (as viewed in FIG. 30) extending generally half-way across the width of slot 554, as measured between side or transverse surfaces 560 and 562, as to have the undersurface 576 (FIG. 31) of such left end generally juxtaposed to the slot 554. The remaining clearance or space, as measured from end 578 of abutment portion 574 to side surface 560, is sufficient to permit a shield plate 580 to be received therethrough. The second 564 and third 570 slots having their side surfaces generally coplanar with respective side or transverse surfaces 560 and 562, permit portions of the shield plate to also be received in each of such slots 564 and 570 and end surface 568, of the second slot 564, serves as an abutment to, at that point, stop the further downward movement (as viewed in FIG. 31) of the shield plate 580. When the shield plate 580 is thusly abutted against end surface 568, the upper edge 581 of shield plate 580 has sufficient clearance to pass under surface 576 of the extension of upper abutment portion 574. Accordingly, with the shield plate 580 being thusly received by slots 554, 564 and 570, if then the adapter body 542 is placed upon the outer cylindrical surface 544 of generally tubular cone 472 and axially slid therealong, the end 582 of the tubular cone 472 will eventually engage the shield plate 580 and ultimately push and hold shield plate 580 between said end 582 and transverse or side surface 562 as well as against the respective coplanar side surfaces of both slots 564 and 570. With the shield plate thusly held, it becomes effectively locked against unintentional withdrawal by the juxtaposed abutting surface 576. As best seen in FIG. 31 an aperture or window-like opening 584 is formed through shield plate 580 which may be formed of lead. In the embodiment illustrated the aperture 584 is of generally rectangular configuration and centrally located as with respect to the central axis of radiation as represented at 586. However, it should be made clear that other configurations and relative locations of such aperture means 584 are contemplated. Further, it is also contemplated that a series of radiation shielding plates may be employed with such series differing from each other primarily in either the configuration, size and/or relative location of the respective aperture means 584 formed in the respective shielding plates comprising the said series of radiation shielding plates. This, of course, would enable the selective use of any of said series of radiation shielding plates for any particular X-ray procedure.

As a general rule, the cone 472 of an X-ray machine has an axially extending reference line 588, often of considerable width, painted or otherwise formed on the outer cylindrical surface 544 at the top thereof as partially shown in FIG. 27 and as generally depicted in phantom line in FIG. 30. (In FIG. 27, the remainder of the reference line 588 is illustrated in relatively heavy dash-like since such would be under the top portion of adapter body 542 but seen therethrough if such adapter body 542 were formed of transparent plexiglass.) Such reference line 588 always remains at the top-most portion of cone cylindrical surface 544 regardless of the position to which such cone is selectively moved. The adapter means body 542 has a series of gauge or reference marks 590, 592, 594, 596 and 598 formed thereon and in the embodiment illustrated such respectively correspond to 0°, 15°, 30°, 45° and 60° of relative angular rotation of the adapter body means 542 with respect to the cone cylindrical surface 544 and index line or means 588. That is, as lines or reference marks 590, 592, 594, 596 and 598 are respectively selectively aligned with gauge line means 588, the indication would be that the adapter body 542 was, respectively, either not relatively rotated or rotated 15°, 30°, 45° or 60° from the position depicted in FIGS. 30 and 31.

The adapter means 538 is also comprised of holder means 600 which may be integrally formed with or fixedly carried by adapter body 542. In the embodiment illustrated, the holder means 600 comprises a cylindrically tubular member 602 having an axis 604 which is parallel to the axis 586.

As generally depicted in FIG. 27, the inner cylidrical surface 606 of member 602 is such as to at least closely receive therein a portion of an alignment rod means 608. Although not shown, the portion 607 of the rod means 608 received by the holder 600 may be suitably keyed thereto to prevent relative rotation.

Alignment rod means 608 is also preferably provided with spacer-like gauging means 610 and 612 each of which may be carried by the alignment rod 608 as by passing therethrough. The spacer gauges 610 and 612 may be respectively provided with suitable abutment surfaces 614 and 616 which may be, for example, of a configuration and size mating with the outer diameter or outer surface of measuring rod 532. Assuming such abutment surfaces to be of cylindrical configuration against which the measuring rod 532 would seat, the distance from the axis 134 to the axis 604, at such seating would be the same as the distance between axis 604 within holder means 600 and the central axis of radiation 586 (FIG. 31) Therefore, once the measurement $L_3$ has been established, the X-ray head is angularly and/or laterally adjusted until the spacer gauges 610 and 612 have their surfaces 614 and 616 engage the measuring rod 532 thereby establishing that the central axis 586 of the X-ray will be in alignment with the transporionic axis 134. Also, spacer gauging means 610 and 612 may be suitably keyed to alignment rod means 608 as to preclude relative rotation therebetween.

As will be noted in both FIGS. 27 and 28, the adapter means 538 is illustrated as having been rotated 15° relative to cone 472 thereby resulting in the aperture means 584, in radiation shielding means 580, being inclined 15° as generally depicted in FIG. 28. It should be mentioned that in the preferred embodiment, the shielding plate means 580 is of a square outer configuration thereby enabling the placement of the shield means 580 as to have the aperture 584 positioned as depicted in FIG. 31 or positioned as to be in effect rotated 90° (about axis 586) from the position shown in FIG. 31.

Considering FIGS. 27, 28, 29, 30 and 31 in conjunction with FIGS. 4 and 11, it will be seen that in the preferred embodiment angulation or inclination indicating means 620 is carried by the arm 180. Such indicating means 620 is illustrated as comprising a dial-like portion 622 carrying thereon a plurality of angular indicator lines or angular graduations radiating from the axis of a pivot means 624 which, in turn, freely pivotally supports a gravity-positioned swingable indicator arm 626. The various angular graduations are preferably provided with juxtaposed numbers (such as, for example: 0, 15, 30, 45 and 60) indicating the magnitude of the juxtaposed radiating graduation. When the cephalostat 10 is horizontally positioned, as depicted in FIG. 4, the indicator arm 626 would be pointed directly downwardly toward the "0" angular designation thereby indicating that the cephalostat 10 is in fact horizontally positioned.

However, as previously described and as depicted in FIG. 11, there are situations in which it is desirable that the cephalostat be inclined from the horizontal. When the cephalostat 10 is thusly selectively inclined, the X-ray film cassette or cassettes carried thereby also become inclined to the same degree. Therefore, if an X-ray exposure were to be made under such circumstances the resulting outline of the exposed area obtained would appear to be angularly misaligned with respect to the film boundary. The use of the adapter means 538 and shield collinator or aperture 584 eliminates such undesired exposure angularity on the X-ray film. For example, if it is assumed that when the cephalostat 10 was adjusted to the inclined position depicted in FIG. 11, the indicator arm 626 (FIG. 4) would have indicated "15" (meaning 15° of inclination) and the procedure as depicted in FIG. 27 was being undertaken, the adapter means 538 would be correspondingly rotated 5° relative to the cone 472 (as depicted in FIG. 27) thereby correspondingly rotating the collinator or aperture 584 15° to a position as depicted in FIG. 28. The resulting position of aperture 584 would then correspond to the position of the X-ray film to be exposed. Once such adjustment and measurements were made (FIGS. 27 and 28), it would be preferred that the measuring or gauging rod means 532 and spacers 610 and 612 (if such were employed) would be removed and the four-bar linkage (comprised of 156, 178, 172) be swung out of the path of the X-ray (in the manner corresponding to FIG. 26) after the pivot member 182 is first axially drawn away from arm 124 and locator 132, before the X-ray exposure were actually made.

In view of the description thus far presented, it should be apparent that the angularity or inclination indicating or gauging means 620 will always indicate the true position of the cephalostat 10, regardless of the selective adjustment of the four-bar linkage means (comprised of 148, 178, 172) because arm 180 under all conditions of adjustment continues to maintain the same relative angular (may be considered nominally or functionally parallel) position with respect to reference plane or surface 136 even though such arm 180 may be, in its then selected position, relatively higher or lower (in terms of elevation) with respect to said reference plane 136. This, of course, is made possible because arm 180 is fixedly connected to or integrally formed with linkage portion 178. It should also be appreciated that because arm 180 thusly maintains its position relative to reference surface or plane 136, the relative relationships of axes 190 and 196 as well as point 198 (FIGS. 1 and 4) also continue to be maintained. Similarly, because body 294 (FIG. 3) is operatively fixedly secured to linkage portion 274, arm portion and body 294 also maintain their previously described established relationships and, therefore, axis 298 and point 192 (FIGS. 1, 3 and 4) also continue to maintain their previously described relationship regardless of the swingable adjustment of the four-bar linkage means (comprised of 268, 274, 286) via control knob means 142.

Further, with reference to FIG. 11, it should be pointed out that in certain situations the patient may only be able to sit in a chair and be unable to in any way recline as on a table. When such is the case, the adjustment means or legs 318 and 320 may, for example, be fully extended as to thereby be able to in effect hang the cephalostat 10 onto to and from the back of a chair and have member 14 against the back rest or support of such chair thereby enabling the patient to sit in such chair and still have the patient place the patient's head against the reference plane or surface 136 in order to perform the desired X-ray procedures. In this connection the angulation or inclination indicating means 620 (FIG. 4)

and the adapter means 538 would be employed as previously described.

Figure 34:
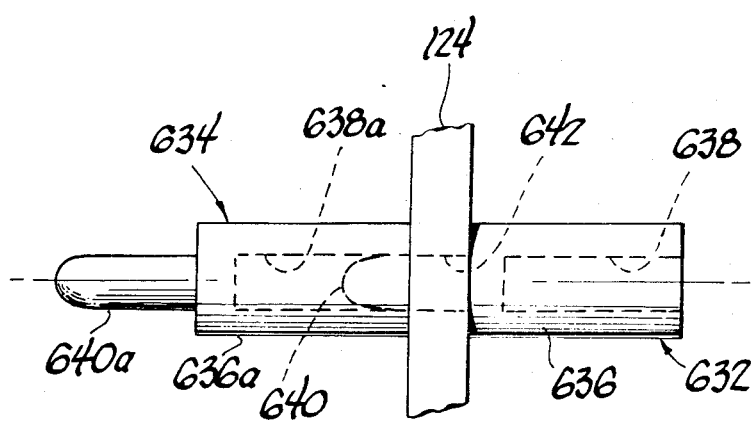
FIG. 34 is a generally elevational view illustrating the adapter means of FIG. 33 being carried as in a stored condition, by one of the elements shown in FIG. 33 (as well as in FIG. 1)
Figure 33:
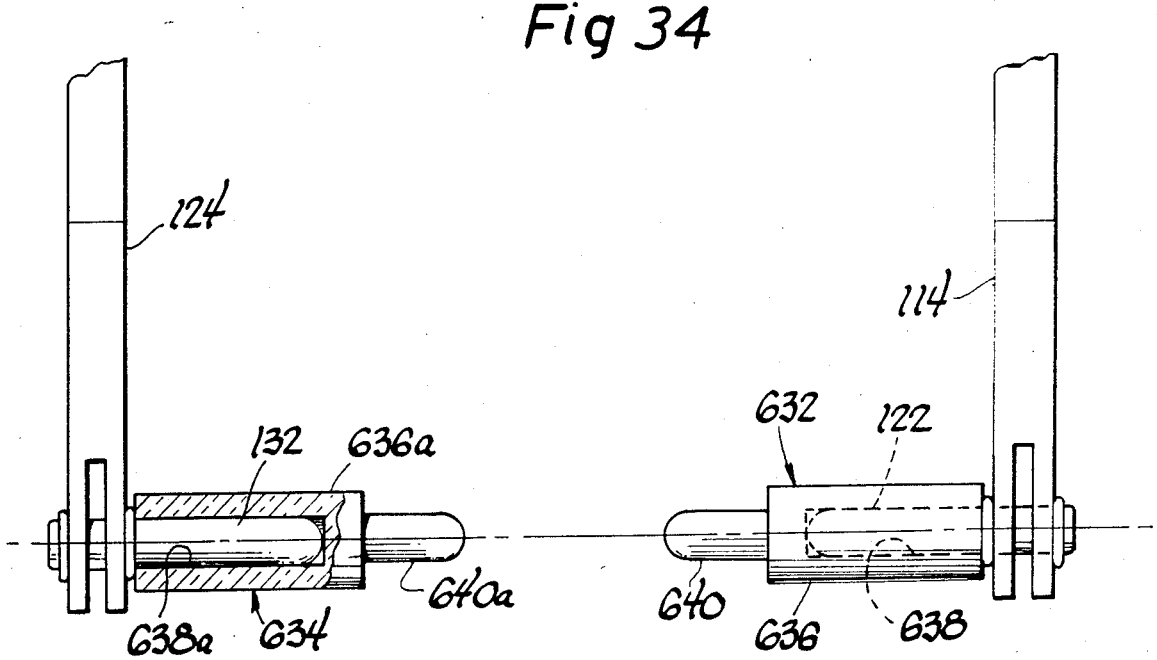
FIG. 33 is a relatively enlarged view of a fragmentary portion of certain of the elements in FIGS. 1, 2 and 3, along with adapter means employable therewith.

Referring in particular to FIGS. 32, 33 and 34, when it is desired to obtain an X-ray image of the patient's submental-vertex, with the cephalostat 10 generally in the position depicted in FIG. 32, and previously referred to with respect to FIG. 14 and axis 342 depicted therein, the related X-ray film cassette is placed generally between the locating arms 114 and 124 and generally against edge 27 and way 56( as already described with respect to FIG. 14; also see FIG. 1). Such X-ray film cassette is schematically depicted in phantom line at 630 of FIG. 32. Such X-ray film cassettes, as at 630, are usually of a standard size which often require the locating arms 114 and 124 to be moved away from each other (in order to accommodate the cassette 630 therebetween) such a distance as to, in turn, preclude such locating arms 114 and 124 from being moved toward each other a distance sufficient to have the ear canal locators 122 and 132 be properly operatively received by the patient's respective ear canals. Accordingly, it is contemplated that additional extension-like ear canal locators 632 and 634 be employed as in combination with ear canal locators 122 and 132, respectively, as to enable the patient's ear canals to be properly located when such cannot be achieved merely by the use of locators 122 and 132 and the attendant sufficient inward movement of arms 114 and 124.

With particular reference to FIG. 33, a relatively enlarged view of a fragmentary portion of the locating arms 114 and 124, it can be seen ear canal locator extension 632 is illustrated as comprising, preferably, a main cylindrical body portion 636 having a centrally located axially extending passage portion 638 of a size as to receive ear canal locator therein The body portion 636, in turn, carries a centrally or axially situated cylindrical extension portion 640 which, preferably is of dimensional characteristics as that of locator 122, serves as one of the patient's ear canal locators. Similar portions and/or elements of extension means 634 and as such relate to primary locator 132 are identified with like reference numbers provided with a suffix "a".

When such canal locator extension means 632 and 634 are not needed, such may be carried, as in storage, by aperture or passage means 642 as of locating arm 124. More specifically, referring to FIG. 34, the aperture or passage 642 slidably receives therethrough, for example, locator extension portion 642 which extends some substantial distance to the left (as viewed in FIG. 34) of arm 124 and is closely received by the passage portion 638a of extension means 634. The body portions 636 and 636a may be respectively abutted against opposite sides of arm 124 and remain in such a stored position until needed to function as in FIG. 33.

Figure 37:
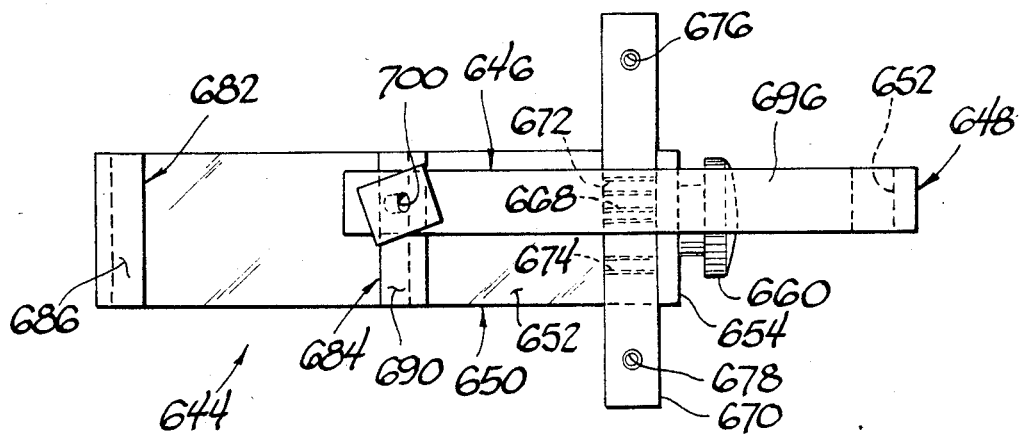
FIG. 37 is a view taken generally on the plane of line 37—37 of FIG. 35 and looking in the direction of the arrows.
Figure 36:
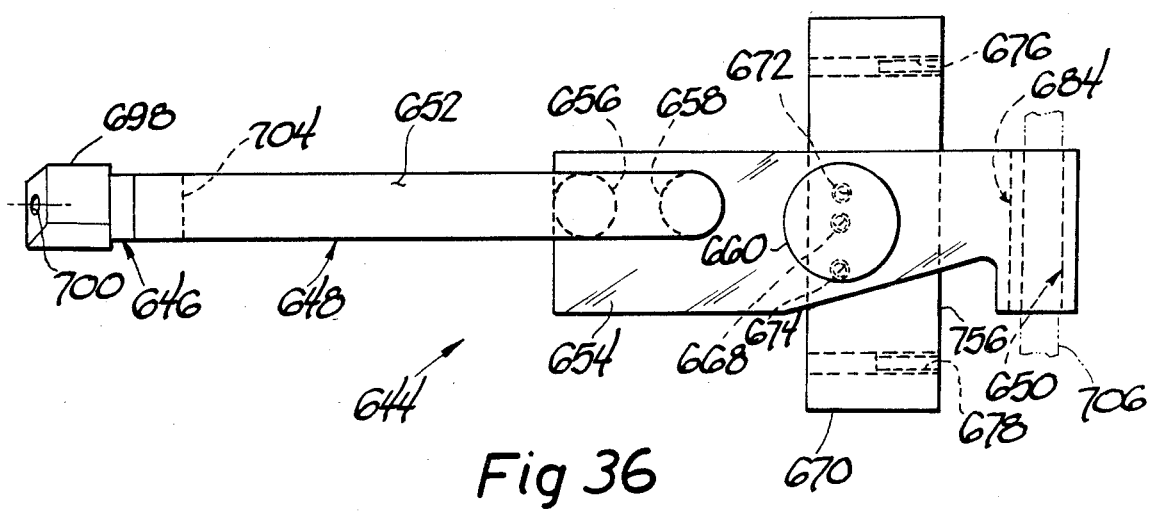
FIG. 36 is a view taken generally on the plane of line 36—36 of FIG. 35 and looking in the direction of the arrows.
Figure 35:
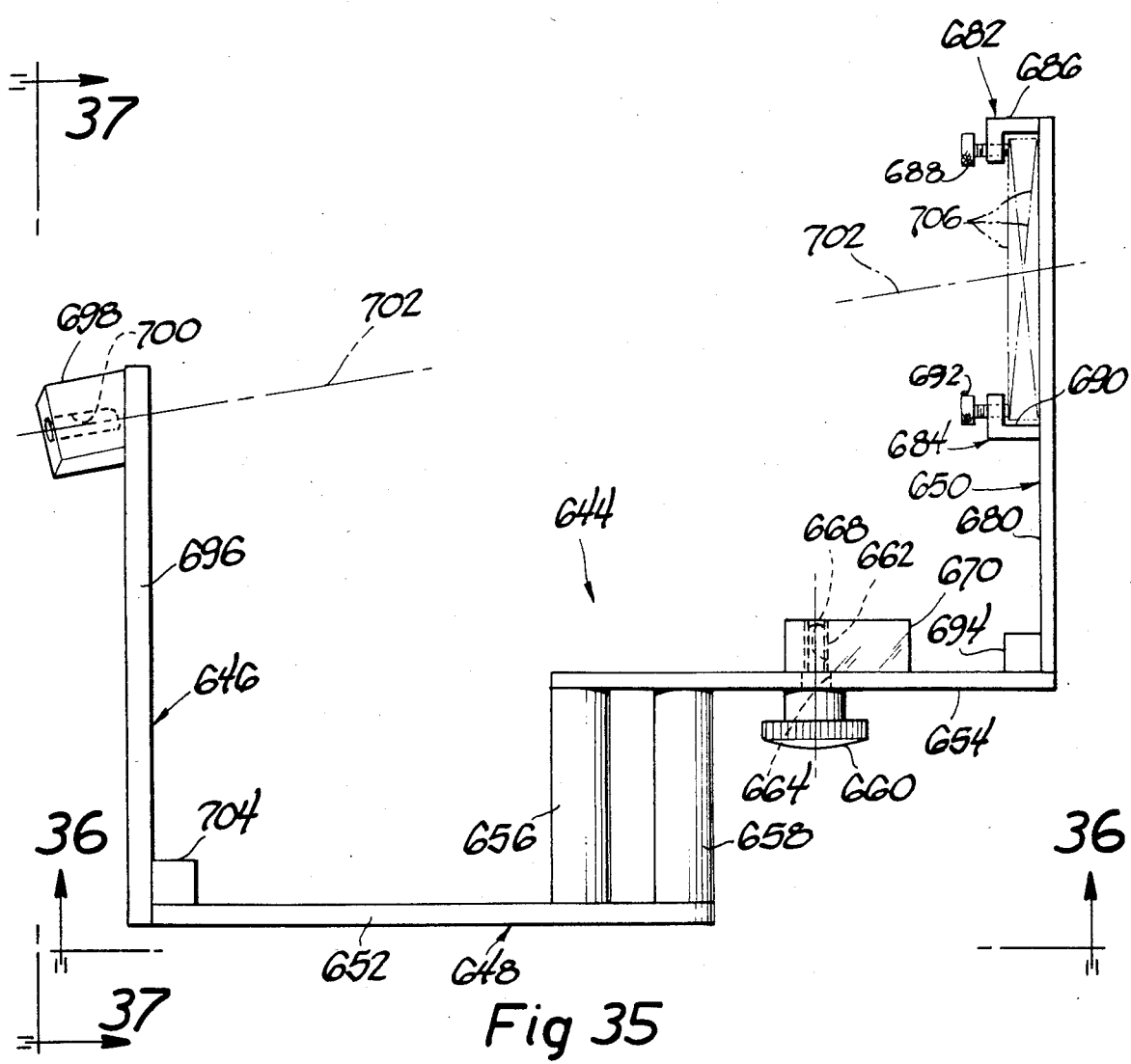
FIG. 35 is a generally top plan view of adaptive support structure which may be employed in combination with the apparatus of FIGS. 1-7.

Referring to FIGS. 35, 36 and 37, it is further contemplated that the preferred embodiment of the cephalostat 10 be effective for carrying arm-like support means 644 for enabling the taking of either a continuous panoramic or intermittent steroscopic X-ray exposure of, for example, a patient's temporomandibular joint.

The preferred embodiment of the support means 644 is illustrated as comprising a plurality of arm means 646, 648 and 650 all operatively interconnected. Arm means 648 is depicted as comprising a first arm body portion 652 rigidly fixedly secured to a second arm body portion 654 as by generally transverse interconnecting structural members 656 and 658. A securing and pivot knob assembly 660, provided with a threaded shank portion 662 passes through a clearance aperture or passage 664 formed in arm body 654 as to threadably engage a threaded hole 668 in a support or mounting block 670. As shown in FIGS. 36 and 37, the block 670 is preferably provided with additional threaded holes 672 and 674, each effective for threadable engagement with threaded shank 662, thereby enabling the knob assembly 660 to be engaged with any of such threaded holes 668, 672 or 674 to provide for a selection of height as may be required.

The support or mounting block 670 is also provided with a pair of generally horizontally extending threaded passages 676 and 678 spaced from each other.

The arm means 650 is illustrated as comprising an arm member 680 which, in turn, carries bracket or clamping means 682 and 684. The clamping or holding means 682 may be comprised of an L-shaped bracket or arm 686, fixedly secured to the arm member 680, and manually adjustable securing means 688 such as a screw or the like. Similarly, holding means 684 is illustrated as comprising an L-shaped bracket or arm 690, fixedly secured to the arm member 680, and manually adjustable securing means 692 such as a screw or the like. A structural reinforcing member 694 may be fixedly secured to both arm members 654 and 680, as at the juncture thereof, to enhance the strength and rigidity of the interconnection of said arm members 654 and 680.

Figure 38:
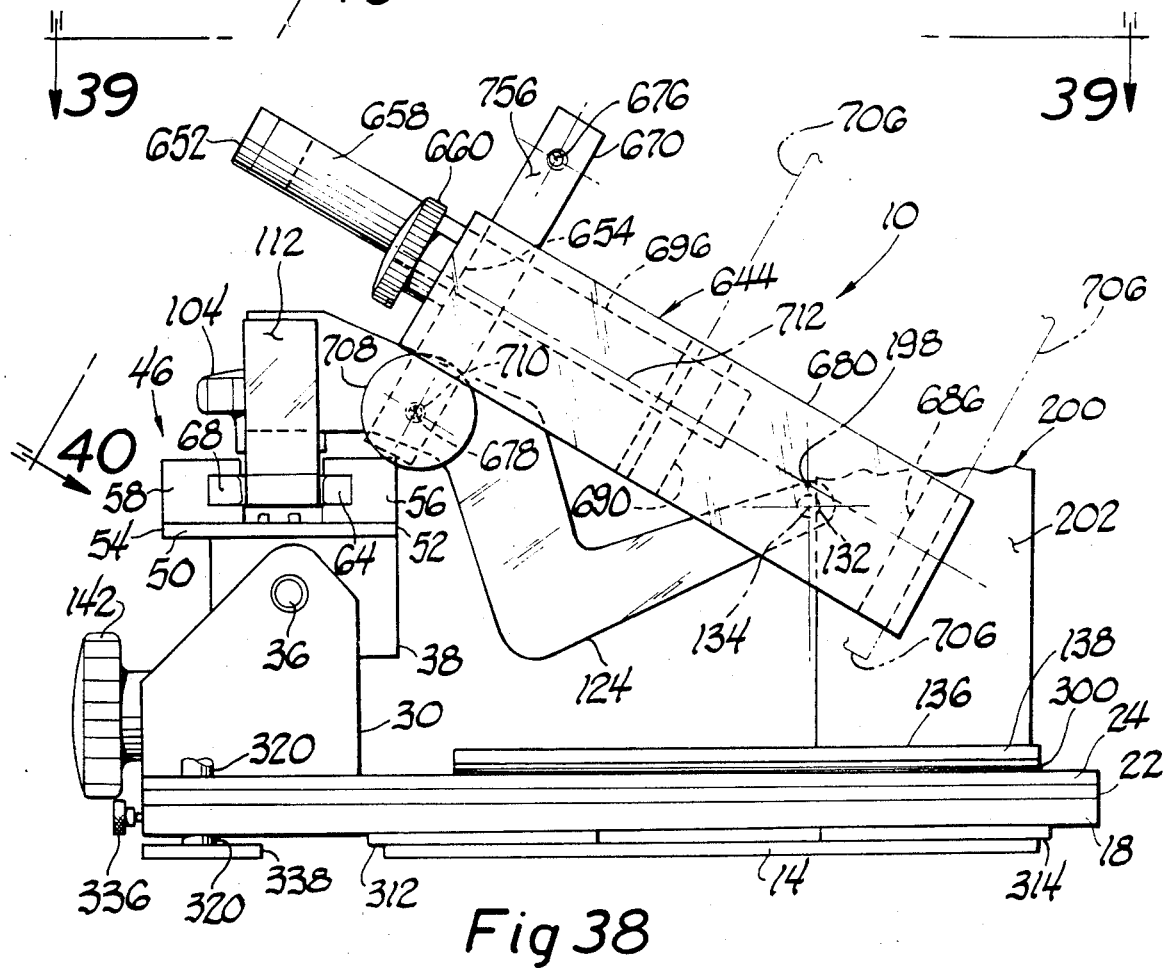
FIG. 38 is a view similar to FIG. 3, with certain elements shown in FIG. 3 being removed for purposes of clarity, and showing the adaptive apparatus of FIGS. 35-37 assembled thereto.
Figure 39:
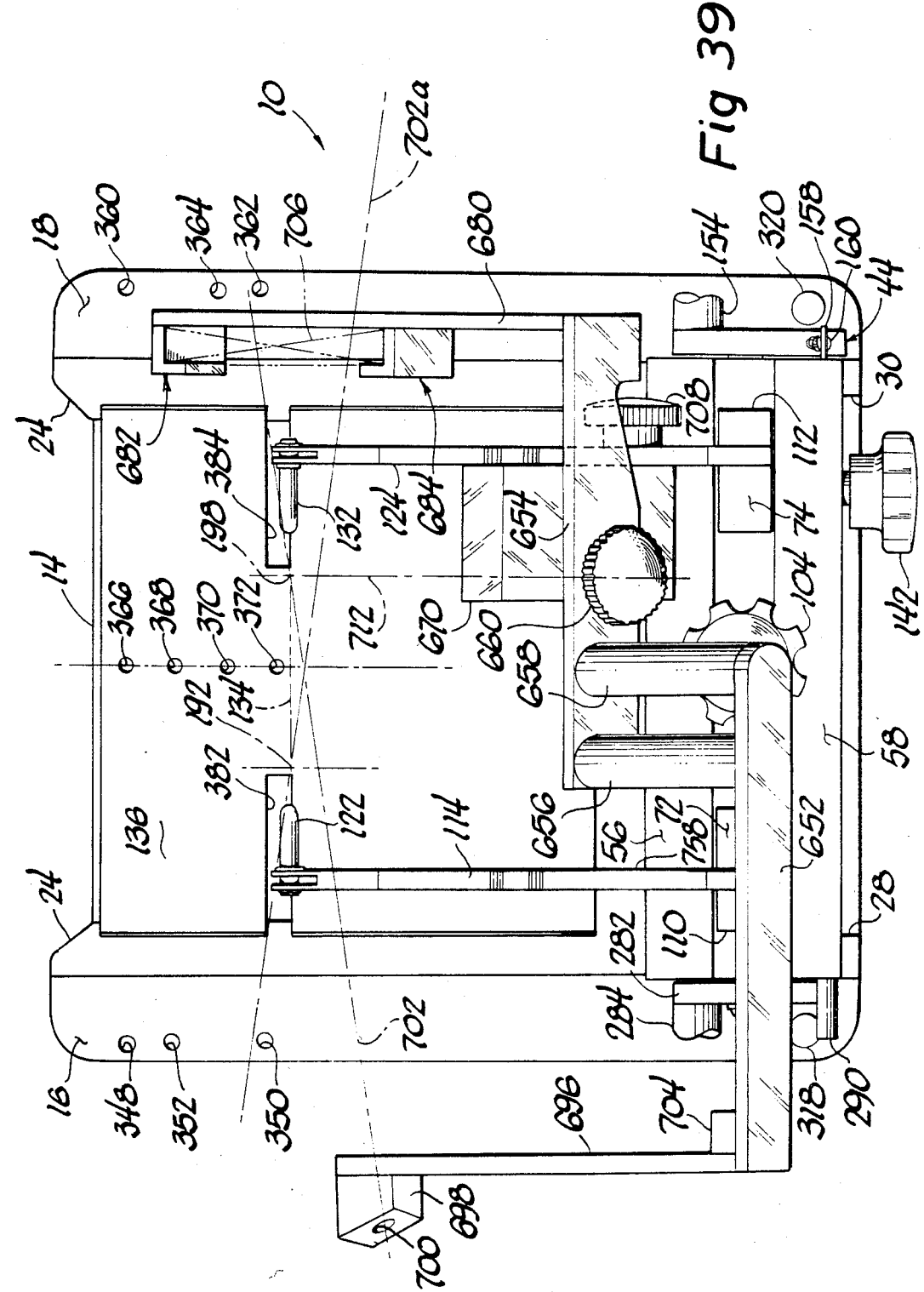
FIG. 39 is a view taken generally on the plane of line 39—39 of FIG. 38 and looking in the direction of the arrows.

Arm means 646 is illustrated as comprising an arm body 696 and a body 698 fixedly carried thereby. The body 698 is provided with aperture or passage means 700 the axis 702 of which, when viewed as in FIG. 35, passes generally through the midpoint of the space generally between clamping or retaining means 682 and 684. Passage 700 is also inclined at a second angle which, in the preferred embodiment, when the arm means 644 is positioned as generally depicted in FIGS. 38 and 39, forms an angle in the order of 18° with the transporionic axis 134. A structural reinforcing member 704 may be fixedly secured to both arm members 652 and 696, as at the juncture thereof, to enhance the strength and rigidity of the interconnection of said arm members 696 and 652.

The clamping or holding means 682 and 684 are effective for supporting therein an X-ray film cassette shematically illustrated by the phantom lines at 706. Once such cassette 706 is detachably secured to arm means 650, the cassette 706 and arm means 650 will move in unison.

Figure 40:
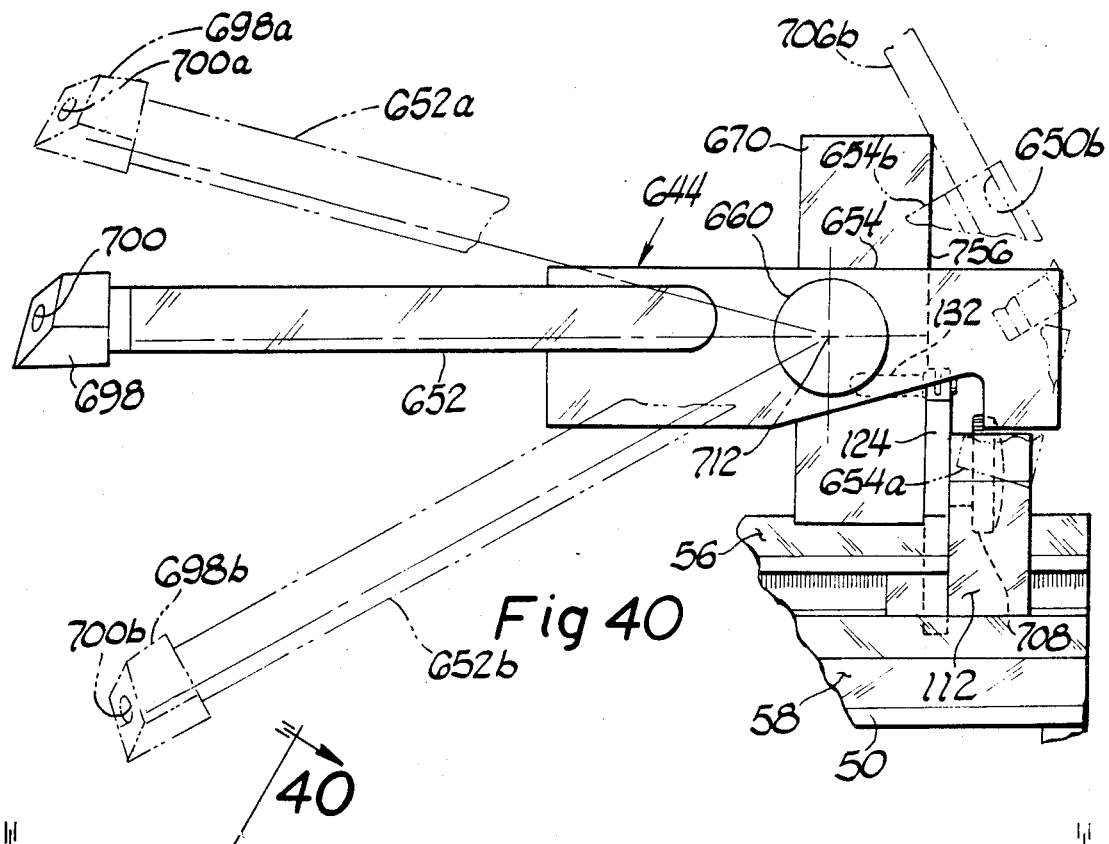
FIG. 40 is a view taken generally on the plane of line 40—40 of FIG. 38 and looking in the direction of the arrows.

FIGS. 38, 39 and 40, illustrate the arm or support means 644 is assembled relationship to the remainder of the cephalostat 10. In assembling the support means 644, the support block 670 may first be secured to and against the inner side of locating arm 124 as by a securing knob means 708 (FIGS. 38, 39 and 40) comprising a threaded shank portion 710 (FIG. 38) which freely passes through, for example, aperture or passage means 642 (FIG. 34), in locating arm 124 and threadably engage, for example, lateral or horizontal threaded passage 678 in support block 670. The knob means 708 may then be tightened as to maintain the support block 670 as in the position generally depicted in FIG. 38. Following this, the support arm means 644 may be secured to the support block 670 as by the threaded shank 662 of knob means 660 passing through aperture means 664 and threadably engaging, for example, threaded passage 668 in support block 670. Generally when the arm support means 644 is thusly secured, the block 670 is so adjusted as to cause the centerline or axis of rotation 712 to pass above the transporionic axis 134 at a height as that represented by, for example, point 198. Further, with the average adult, the axis 712 of rotation will also be displaced, laterally, of the mid-sagittal plane in the order of 2.0 inches. With the support lever means 644 is a generally horizontal position, that is with angular movement about axis 712, the top plan view thereof would be as generally depicted in FIG. 39 while the side view would be as generally depicted in FIG. 38.

Although the practice of the invention is not so limited, in the preferred arrangement of the invention, elements such as, for example, 14, 16, 18, 22, 24, the four-bar linkage means on either side, 122, 132, 114, 124, 182, 204, 234, 244, 462 and 644 would be formed as of a clear plexiglass while, for example, a high molecular weight polyethylene would preferably be used as for the ways 56, 58, block 135 and trunnions or pivot supports 28 and 30. The various gears are commercially available as stock items and the respective ratios etc. would, in the main, be a matter of personal choice.

As already generally described, the invention has the capability of receiving and positioning various X-ray film cassettes for respective various procedures. For example: a first X-ray film cassette 236 can be held by vertical support arm means 200, at the left side (as viewed in FIG. 1), and a second (or same yet unexposed) film cassette can be held by the vertical support means 200 when, and if, such is transferred to the right side (as viewed in FIG. 1); a third X-ray film cassette 304–306 may be situated directly below surface 168 (FIG. 5) and thereby behind the back of the patient's head; a fourth X-ray film cassette 630 may be situated behind the top of the patient's head (FIG. 32) and additional X-ray film cassettes can be carried and positioned as by the holder means 386 (FIGS. 19–23).

Operation of the Invention

Most of the overall operation of the invention has already hereinbefore been discussed as part of the description of the various elements and their inter-actions. The following, therefore, is primarily to further discuss certain aspects of the operation already presented and/or discuss certain operations and/or features not yet specifically discussed.

In the following, in addition to FIGS. 1–31 and 33–40, reference will also be made to FIGS. 32 and 41.

Figure 41:
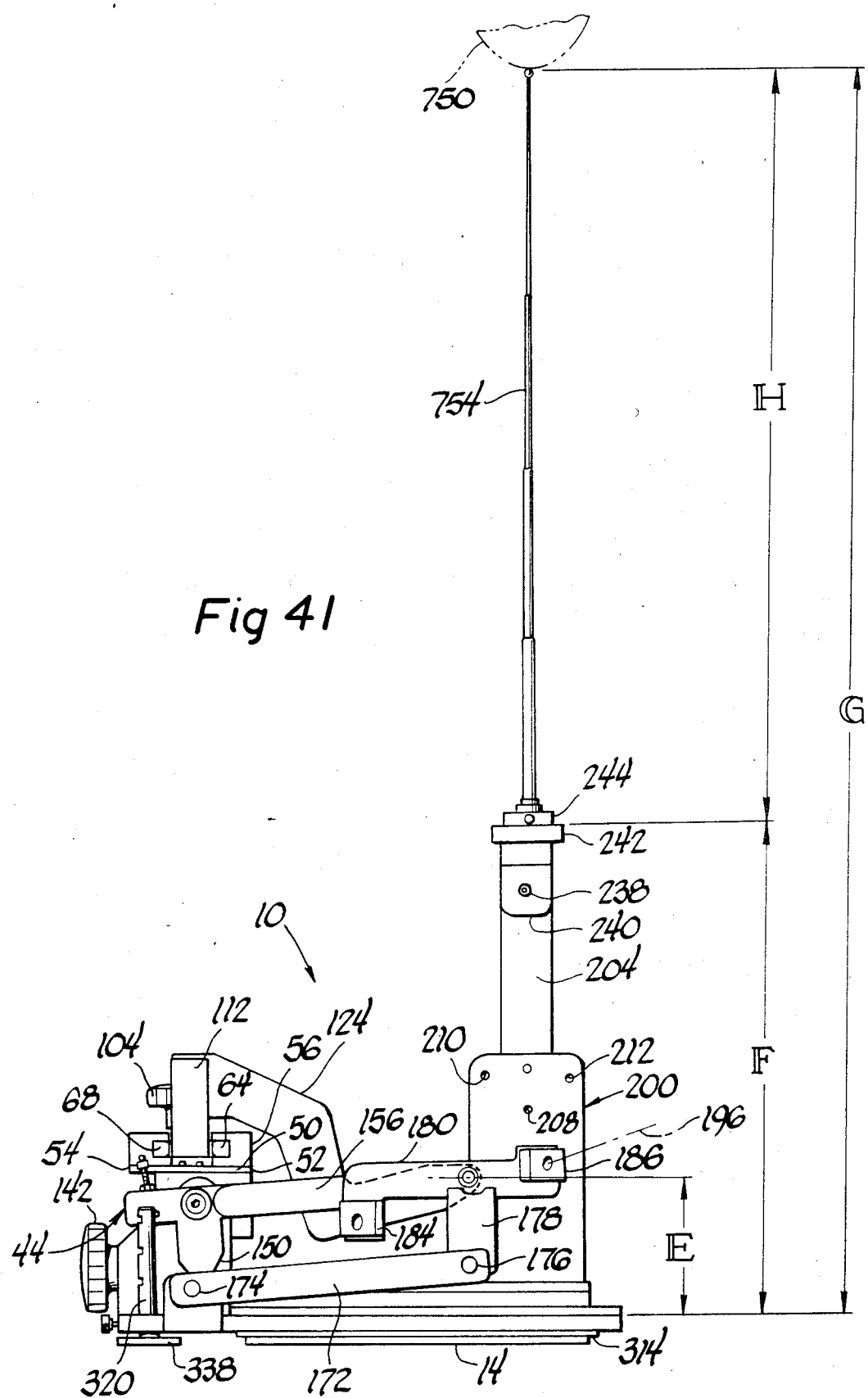
FIG. 41 is a view similar to that of FIG. 4, in reduced scale and with considerably less detail, illustrating the apparatus of the invention as it may appear prior to the exposing of the unexposed film situated below the patient's head.

FIGS. 32 and 41 are somewhat respectively similar to FIGS. 1 and 4 with the exceptions that FIGS. 32 and 41 are each of a relatively reduced scale and only so many of the elements (some somewhat simplistically illustrated) are shown as is believed necessary to convey the interrelationships thereof and the overall operation of the invention.

Referring in greater detail to FIGS. 32 and 41, in one successful embodiment of the invention, the mid-distance between the locating members 122 and 132 when measured to the plane of the cassette film 236 was established at a dimension, A, which, in the preferred embodiment was established to be 15.0 cm. Accordingly, after a patient's head is placed on the plate or member 138 as to have the back or posterior portion of that patient's head rest on reference surface 136, control means or knob 104 is rotated in a direction as to cause the locating arms 114 and 124 as well as locating members 122 and 132 to move relatively toward each other. The locating members 122 and 132 are, as already indicated, plug-like members adapted to be received in the external auditory canals, or porionic canals, of the patient. Therefore, such locating members 122 and 132 are moved generally inwardly toward the patient's auditory canals along with such adjustments as are necessary with knob 142 to place such locating members at the proper elevation to be received by the patient's auditory canals.

At this time certain factors are established; that is, the mid-sagittal plane of the patient has been established as existing parallel to the film in the cassette 236 (if such is actually being employed) and at a fixed dimension, A, away from the film of such cassette; the other is that the patient's transporionic axis has also been established as being axially aligned with axis 134 of locating members 122 and 132 which is also coaxial with means 182 of the four-bar linkage means, at the right side of the cephalostat 10 as viewed in FIG. 1.

In order to obtain a lateral X-ray exposure of the patient's head, all that is further necessary is to first axially slide member 182 into operative engagement with locating arm 124 and member 132 (as previously described with reference to FIG. 27) and bring the anode (schematically depicted in FIG. 32 as at 750 and functionally equivalent to cone 472 of FIGS. 27, 30 and 31) of the related generally standard X-ray machine into alignment with the transporionic axis 134 and, preferably after swinging the four-bar linkage means upwards and rearwardly, cycle such X-ray machine for the desired exposure time. However, in many instances, it is desired to establish a particular degree of magnification which will be again used in subsequent cephalograms especially for purposes of comparison. With the invention, this becomes very simple. That is, since the dimension, A, is fixed, the selected degree of magnification (as also hereinbefore generally discussed with reference to FIG. 27) becomes a simple matter of mathematics. That is, the distance $A+B+C$ (the total distance from the p lane of the film to the anode 750 of the X-ray machine) divided by the distance $B+C$ will give the resulting degree of magnification. Therefore, in the invention, with dimension A being fixed and dimension B being determinable (upon member 182 being first operatively engaged with locator arm 124 and ear canal locator 132), it becomes a simple mathematical equation to determine the dimension, C, in order to acheive the desired degree of magnification. This can be achieved as by having gauging or measuring rod means 532 of FIG. 27 of an extendible configuration. That is, with means 182 being in operative engagement with locator arm 124 and locator plug 132, and the dimensions A and B now being known, all that has to be done is to operatively secure the extendible rod or gauging means 532 to and in axial alignment with means 182 and extend such gauging means 532 until it attains the proper calculated length, C, and then bring the anode 750 (as, for example, cone 472) of the X-ray machine into alignment therewith and in touching or otherwise proper relationship (as generally discussed with reference to FIG. 27) to the free end of the gauging means 532 after which, the means 182, first being pulled back out of operative engagement with arm 124 and locator 132, and measuring rod or means 532 are preferably swung upwardly (generally counter-clockwise as viewed in FIG. 4) and the X-ray machine cycled for the appropriate time span thereby exposing the film in the cassette 236. As generally indicated with reference to FIG. 27, the adapter means 538 and collimator means 580 may or may not be employed depending upon choice.

Once the patient's head has been located as described above, the graduations on gauge means 164 are checked to see which of such graduations 752 is, for example, juxtaposed to the pointer 162. If, for example, the juxtaposed graduation is "12", that would mean that dimension, E, (FIG. 41) is actually 12.0 cm. away from the plane of the film in the cassette 304–306 (FIGS. 5 and 12). If it is desired to establish a particular degree of magnification which will be again used in subsequent cephalograms, especially for purposes of comparison, such becomes a very simple mathematical equation with the invention. That is, since dimension, E, is established by virtue of the rotation of the platform or carrier means 46 and locators 122, 132, and therefore for that patient at that time, fixed, the selected degree of magnification becomes a simple matter of mathematics. That is, the distance H and F (the total distance from the plane of the film of cassette 304–306 to the anode 750 of the X-ray machine) divided by the distance G-C will give the resulting degree of magnification. Therefore, in the invention with dimension, F, being fixed and dimension, E, being determinable (scale or gauge means 164), it becomes a simple mathematical equation to determine the dimension, H, in order to achieve the desired degree of magnification. This can be achieved as by the use of an extendible or telescoping rod means 754 which is detachably securable to the arm 244 as at aperture 248 (FIG. 1). That is, with the axis of aperture 248 being aligned with the mid-sagittal plane and fixed dimension, F, being known, less the determinable dimension, E, all that has to be done is to attach the extendible measuring rod 754 to arm 244, in aperture 248 thereof, and extend rod means 754 until it attains the proper calculated length, H, and then bring the anode 750 of the X-ray machine into alignment with rod 754 and in touching or other operative relationship therewith after which the arm 244, arm 204 and rod 754 may be swung as to a position (for example as in FIG. 14 or opposite thereto) out of the line of action of the X-ray machine and the X-ray machine cycled for the appropriate time span thereby exposing the film in the cassette 304–306.

FIG. 32 also depicts the use of the expandible or telescoping rod means 754 detachably secured to arm 244 and positioned as to be in the mid-sagittal plane which would contain axis 342. This particular position is also at least partly depicted in FIG. 14 wherein lever or arm 204 is indicated as having been rotated from the vertical and detachably locked as to result in the axis 342 being inclined in the order of 8° from the horizontal or reference surface 136. As a consequence the axis 342 is generally perpendicular to the plane of the film in the X-ray cassette 630 (FIG. 32) situated generally between the arms 114 and 124. Once the proper or desired distance to the X-ray anode 750 is determined, in the manner as generally hereinbefore described, the arm 244 and telescoping or measuring rod means 750 may be swung out of the line of radiation (as by, for example, pivoting about either pivot means 246 or pivot means 238) and the X-ray machine cycled for the appropriate exposure time. This, of course, would expose the film in cassette 630 and the image obtained would be the submental-vertex which is a view as if looking at the structure of the patient's head generally in the direction of axis 342 from under the patient's chin to the top of the patient's head. It should be pointed out that the inclination of the measuring rod 754 is also an aid in avoiding any interference with the patient's body in bringing the anode 750 into position.

The taking of exposures of, for example, the left and/or right temporomandibular joints as along axes 190 and/or 298 has already been described, as well as the use of the film cassette holder or carrier means 386, and such will not be repeated here.

As was previously stated with reference to FIGS. 35–40, the arm-like support means 644 enables the taking of either a continuous panoramic or intermittent stereoscopic X-ray exposure of, for example, a patient's temporomandibular joint. Now, assuming that the support means 644 has been attached to the remaining portion of the cephalostat 10, as previously described and as generally depicted in FIGS. 38, 39 and 40, let it be further assumed that the patient's head has been properly situated on the reference plane 136 by the proper adjustment of the arms 114 and 124 and ear canal locators 122 and 132 (as previously described with reference to other procedures performed with cephalostat 10). An associated X-ray film cassette 706 would then be suitably secured by clamping or securing means 682 and 684 as to thereby be secured to arm member 680 as to be movable in unison therewith. In the preferred arrangement, gauging and alignment means 462 (FIGS. 24, 25 and 32) would be operatively connected to passage portion 700 as, for example, in the manner depicted in FIG. 32. Such gauging and alignment means 462, as previously described with reference to, for example, FIG. 24, enable the anode 472 (FIG. 24), schematically depicted as at 750 of FIGS. 32 and 41, to be placed as against surface 474 to thereby align the X-ray radiation with axis 702 (FIG. 35).

Now with particular reference to FIG. 40 and assuming that the said alignment and gauging means 462 is situated as to be operatively connected in passage 700, let it be further assumed, for purposes of description, that the entire support assembly 644 is pivotally rotatable about axis 712 as from a first extreme position, fragmentarily depicted in phantom line with the various elements thereof being identified with reference numbers provided with a suffix "a", to a second extreme position which is fragmentarily depicted in phantom line with the various elements thereof being identified with reference numbers provided with a suffix "b". In the arrangement of FIGS. 38, 39 and 40, the patient's right tempor-mandibular joint is to be X-rayed. With the arm in position as depicted in 652a (assumed to be the starting position) the X-ray film cassette 706 will be at its lower most position as determined by arm portion 654a which, as disclosed, operatively carries arm 680 and the X-ray film cassette 706. In the procedure wherein a continuous panoramic irradiation is desired, with the X-ray anode being held as against the surface 474 of gauging and alignment means 462 the entire support means 644 is rotated (while maintaining the cycled X-ray anode aligned with surface 474 and axis 702) from the position as depicted, for example, at 652a to the position depicted at, for example, 652b at which time the X-ray source is de-energized. When the support means 644 thereby reaches the position at 652b, it will be noted that arm portion 654b and X-ray film cassette 706b have pivotally reached their corresponding highest position. As a consequence of such irradiation being made, in the assumed continuous panoramic mode, about the axis 712 which in effect passes through the patient's right temporomandibular joint, a very clear image of the joint structure is obtained because the panoramic movement of the irradiation in effect causes the tissue, etc. surrounding the said joint to become greatly if not toally faded-out ("washed-out") thereby providing a sharp image of the said joint.

As already mentioned, the support means 644 may also be employed for conducting an intermittent stereoscopic X-ray exposure procedure. Such would be conducted in the manner herein already described with regard to conducting the continuous panoramic mode with the following exception. That is, if for purposes of description it is assumed that the total angular pivotal rotation (from the position depicted at 652a to the position depicted at 652b is 45°, the irradiation would not take place continuously over through such a 45° sweep. Instead, assuming a total exposure or irradiation time of four-fifths of a second is desired, a first one-fifth second exposure could be taken with the support means 644 in the position depicted at 652a; the support means 644 could then be rotated counter-clockwise (as viewed in FIG. 40) 15° and a second one-fifth second exposure could be taken; the support means 644 could then be rotated counterclockwise an additional 15° and a third one-fifth second exposure could be taken; and finally, the support means 644 could be rotated counter-clockwise the last 15° and the fourth one-fifth second exposure could be taken. Such a stereoscopic irradiation procedure of the tempormandibular joint would also produce a very clear image of the said joint structure because such angular (even though intermittent) irradiation also, in effect, causes the tissue, etc. surrounding the said joint to become greatly if not totally faded-out ("washed-out") thereby providing a sharp image of the said joint.

The support means 644 has been illustrated and described with regard to its use in producing an X-ray image of the patient's right temporomandibular joint. However, it should be made clear that the support means 644 may also be employed for performing either of such X-ray procedures on the patient's left temporomandibular joint. All that needs to be done in order to accomplish such is to threadably disengage the knob 708 from threaded aperture 678 (FIG. 36) of mounting block 670 and then, after removing the support means 644 from the arm 124, rotating the support means 644, as viewed in FIG. 36, 180° so that mounting block 670 becomes at the left side as well as does knob means 660 while arm portion 652, arm portion 696 and body 698 become situated at the right side. With the support means 644 thusly reversed (end-for-end) the mounting block 670 is then brought against locating arm 114 as to have its surface 756 juxtaposed to surface 758 (FIGS. 1 and 39) of locating arm 114 and threaded passage 676 aligned with clearance aperture or passage 760 (FIG. 3) in locating arm 114. (Clearance aperture 760 would be the functional equivalent of passage 642 in locating arm 124.) The threaded shank portion of knob means 708 would then be inserted through clearance passage 760 and threadably engaged with threaded passage means 676 thereby securing the mounting block 670 to locating arm 114. The adjustment, positioning and operation of the support means 644 would then be as hereinbefore described with reference to FIGS. 35–40 (and the axis of radiation would then be as at 702a of FIG. 39) except that now the patient's left temporomandibular joint would be the one being X-rayed.

It should also be mentioned that even though in the preferred embodiment arm means 646 is rigidly secured to arm member 652, it is also contemplated that such arm means 646 may be operatively connected to arm means 652 as by suitable pivotal latching means permitting arm means 646 to be swung away from the path of radiation once the source of radiation has been properly situated.

The invention has been disclosed with the platform assembly 46 being such as to have the locating arms 114 and 124 extending from the top thereof and then generally sweeping downwardly. It is also contemplated that such platform assembly 46 may be made as to have the locating arms extending generally from beneath the platform assembly 46 and ways 56, 58 and then extending generally horizontally to carry, at their respective ends, the ear canal locator plugs.

Although only a preferred embodiment and certain modifications of the invention have been disclosed and described, it is apparent that other embodiments and modifications of the invention are possible within the scope of the appended claims.

What is claimed is:

1. A portable cephalostat, comprising portable body means, first means defining a non-resilient fixed reference plane of elevation carried by said body means and against which the back or a patient's head is to be directly located, second means for locating first unexposed film at a preselected elevation below the back of the patient's head and said fixed reference plane of elevation, third means for locating second unexposed film to the one side of the patient's head when the back of said patient's head is located against said fixed reference plane of elevation, fourth means for guidingly positioning said patient's head along said fixed reference plane of elevation as to thereby have the mid-sagittal plane of said patient's head situated at a preselected distance from said second unexposed film and for determining the elevation above the plane of said first film of the transporionic axis of said patient's auditory canals when the mid-sagittal plane of the patient's head is at said preselected distance, and fifth means operatively connected to said body means for aiming a source of X-ray radiation at a selected angle with respect to said transporionic axis, said fifth means being effective for maintaining said selected angle regardless of the magnitude of elevation of said transporionic axis above said reference plane of elevation, wherein said second means comprises reference surface means carried by said body means, wherein said third means comprises support means carried by said body means, wherein said support means is effective to support said second unexposed film in a generally vertical position generally parallel to said mid-sagittal plane, wherein said fourth means comprises first and second arm-like means, first ear canal locating means carried by said first arm-like means and extending generally toward said second arm-like means, second ear canal locating means carried by said second arm-like means and extending generally toward said first arm-like means, said first and second arm-like means being adjustable throuqh an arcuate path of movement simultaneously toward and awav from said fixed reference plane of elevation as to enable said first and second ear canal locating means to be at an appropriate elevation with respect to said fixed reference plane of elevation as to enable the respective reception of said first and second ear canal locating means by the auditory canals of the patient's head, wherein said arcuate path of movement is about an axis of rotation, wherein said axis of rotation is parallel to said fixed reference plane of elevation, said first and second arm-like means also being simultaneously movable toward and away from each other as to thereby respectively generally contain and release said patient's head.

2. A cephalostat according to claim 1 wherein said first and second ear canal locating means respectively comprise first and second plug-like members, and further comprising first and second plug-like extension members, said first and second plug-like extension members being effective to be at times respectively operatively connected to and carried by said first and second plug-like members.

3. A cephalostat according to claim 1 and further comprising read-out type indicator means, said indicator means being effective to indicate the actual distance above said plane of said first film of said transporionic axis of the patient's auditory canals when the back of the patient's head is located against said fixed reference plane of elevation and the mid-sagittal plane of the patient's head is at said preselected distance.

4. A cephalostat according to claim 1 and further comprising manually operative drive means operatively connected to said first and second arm-like means, said drive means being effective to cause said first and second arm-like means to simultaneously move toward and away from each other.

5. A cephalostat according to claim 4 wherein said manually operative drive means comprises rotary gear means, first gear rack means, second gear rack means, wherein said first gear rack means is in meshed engagement with said rotary gear means at generally one diametral side of said rotary gear means, wherein said second gear rack means is in meshed engagement with said rotary gear means at generally a second diametral side of said rotary gear means generally opposite to said one diametral side wherein said first gear rack means is operatively connected to said first arm-like means, wherein said second gear rack means is operatively connected to said second arm-like means, and wherein upon manual rotation of said rotary gear means said first and second gear rack means are caused to move in directions opposite to each other.

6. A cephalostat according to claim 1 wherein said body means comprises additional support means, carrier means supported by said additional support means, wherein said carrier means is relatively rotatable with respect to said additional support means, wherein said first and second arm-like means are operatively carried by said carrier means as to be generally cantilevered therefrom, and wherein said first and second arm-like means is adjustable through said arcuate path of movement by rotation of said carrier means relative to said additional support means.

7. A cephalostat according to claim 6 and wherein said first and second arm-like means are cantilevered in a manner as to be cantilevered from above said carrier means.

8. A portable cephalostat according to claim 1 and further comprising sixth means for locating third unexposed film at generally the top of the patient's head when the back of said patient's head is located against said fixed reference plane of elevation.

9. A cephalostat according to claim 8 and further comprising angularly positionable support means, distance and alignment gauging means operatively carried by said angularly positionable support means, said angularly positionable support means when positioned in a selected position being effective to correspondingly position said gauging means whereby said gauging means determines a direction generally perpendicular to said third film thereby establishing the proper direction of radiation from the source of X-ray radiation, and wherein said gauging means is also effective for establishing the desired distance as between the anode of said source of X-ray radiation and said third film.

10. A cephalostat according to claim 1 and further comprising sixth means for holding and locating third unexposed film at said one side of said patient's head when the back of said patient's head is operatively located against said reference plane of elevation, said sixth means being effective to hold said third unexposed film at a location generally between where said second unexposed film would normally be situated and said one side of said patient's head, said sixth means being further effective to be moved and hold said third film at a location at the other side of said patient's head opposite to said one side.

11. A cephalostat according to claim 10 and further comprising first keying means carried by said body means, and second keying means carried by said sixth means, said first and second keying means cooperating with each other to determine the location of said sixth means when situated at either said one side of said patient's head or at said other side of said patient's head.

12. A cephalostat according to claim 1 wherein said third means is detachably secured to generally one side of said body means when effective for locating said second unexposed film to one side of said patient's head, and wherein said third means is detachable from said one side of said body means and in turn detachably securable to generally an other side of said body means generally opposite to said one side in order to thereby locate said second unexposed film at the other side of said patient's head generally opposite to said one side of said patient's head.

13. A cephalostat according to claim 12 and further comprising angularly positionable support means, distance and alignment gauging means operatively carried by said angularly positionable support means, said angularly positionable support means when positioned in a selected position being effective to correspondingly position said gauging means whereby said gauging means determines a direction generally perpendicular to said third film thereby establishing the proper direction of radiation from the source of X-ray radiation, wherein said gauging means is also effective for establishing the desired distance as between the anode of said source of X-ray radiation and said third film, and wherein said angularly positionable support means is carried by said third means.

14. A cephalostat according to claim 1 and further comprising sixth means operatively carried by said body means and pivotally rotatable about a second axis passing generally through the patient's temporomandibular joint and in a plane generally perpendicular to said transporionic axis, said sixth means being effective to carry for movement in unison therewith third unexposed film so that upon rotation of said sixth means said third unexposed film rotates in a radius about said second axis generally at one side of said patient's head, said sixth means comprising aiming means effective for aiming the direction of radiation from an associated X-ray source so that the direction of said radiation is from the opposite side of said patient's head passing generally through said temporomandibular joint and exposing said third film as said third film is rotatably positioned about said second axis.

15. A cephalostat according to claim 1 wherein said sixth means comprises rotatable body means, wherein said rotatable body means is pivotally rotatable in a plane generally perpendicular to said second axis, wherein said aiming means comprises arm means operatively fixedly carried by said rotatable body means.

16. A cephalostat according to claim 14 wherein the patient's temporomandibular joint is actually the patient's right temporomandibular joint.

17. A cephalostat according to claim 14 wherein the patient's temporomandibular joint is actually the patient's left temporomandibular joint.

18. A cephalostat according to claim 1 and further comprising sixth means operatively carried by one of said first and second arm-like means and pivotally rotatable about a second axis passing generally through the patient's temporomandibular joint and in a plane generally perpendicular to said transporionic axis when said patient's head is located against said fixed reference plane of elevation and situated at said preselected distance, said sixth means being effective to carry for movement in unison therewith third unexposed film so that upon rotation of said sixth means said third unexposed film rotates in a radius about said second axis generally at one side of said patient's head, said sixth means comprising aiming means effective for aiming the direction of radiation from an associated X-ray source so that the direction of said radiation is from a side of said patient's head opposite to said one side and passing generally through said temporomandibular joint and exposing said third film as said third film is rotatably positioned about said second axis.

19. A cephalostat according to claim 18 wherein said sixth means is operatively carried by either one of said first and second arm-like means.

20. A cephalostat according to claim 1 and further comprising sixth means for selectively adjustably inclining said body means and said first means with respect to an associated supporting means.

21. A cephalostat according to claim 1 and further comprising sixth means for selectively adjustably inclining said body means and said first means, wherein said sixth means comprises leg means movable with respect to said body means, said leg means being extendible downwardly of said body means as to thereby enable said body means and said first means to be inclined with respect to a generally horizontally disposed associated support structure or to be engaged as atop the back support means of an associated chair structure.

22. A cephalostat according to claim 20 and further comprising angular inclination indicator means, said indicator means being effective to indicate the angular degrees of inclination from the horizontal to which said body means and said first means have been selectively adjustably inclined.

23. A cephalostat according to claim 20 and further comprising adjustable collimator means employable in combination with an associated source of X-ray radiation, said collimator means being angularly adjustable with respect to said source of X-ray radiation as to be adjustably angularly positionable to correspond to the degree of angular inclination to which said body means and said first means have been selectively adjustably inclined.

24. A cephalostat according to claim 1 and further comprising retaining means, said retaining means being situated at an elevation whereby said first unexposed film is supported by said retaining means as to thereby assure said first film maintaining said selected elevation below said back of the patient's head.

25. A cephalostat according to claim 1 wherein said fifth means comprises four-bar linkage means, wherein said four-bar linkage means comprises first second third and fourth pivot means, wherein said first and second pivot means are situated generally at one end of said four-bar linkage means as to have fixed pivotal axes, wherein said third and fourth pivot means are situated generally at a second end of said four-bar linkage means as to have translationally swingable axes, wherein said four-bar linkage means comprises a linkage pivotally connected to said third and fourth pivot means, wherein said four-bar linkage means is positionable with said first and second arm-like means as said first and second arm-like means move through said arcuate path, and wherein said linkage carries a radiation aiming portion.

26. A cephalostat according to claim 25 and further comprising aiming adjustment means operatively connectible to said aiming portion as to thereby selectively change said selected angle with respect to said transporionic axis.

27. A cephalostat according to claim 26 wherein said aiming adjustment means is capable of selectively changing in two orders of direction said selected angle with respect to said transporionic axis.

28. A portable cephalostat, comprising portable body means, first means for locating the back of a patient's head at a reference plane of elevation, second means for locating first unexposed film at a selected elevation below the back of the patient's head and said plane of elevation, third means for locating second unexposed film to one side of the patient's head when the back of said patient's head is operatively located against said reference plane of elevation, fourth means for guidingly positioning said patient's head along said reference plane of elevation as to thereby have the mid-sagittal plane of said patient's head situated at a selected distance from said second unexposed film and for determining the elevation above the plane of said first film of the transporionic axis of said patient's auditory canals when the mid-sagittal plane of the patient's head is at said selected distance, fifth means for aiming a source of X-ray radiation at a selected angle with respect to said transporionic axis, said fifth means being effective for maintaining said selected angle regardless of the magnitude of elevation of said transporionic axis above said reference plane of elevation, and sixth means for holding and locating third unexposed film at said one side of said patient's head when the back of said patient's head is operatively located against said reference plane of elevation, said sixth means being effective to hold said third unexposed film at a location generally between where said second unexposed film would normally be situated and said one side of said patient's head, said sixth means being further effective to be moved and hold said third film at a location at the other side of said patient's head opposite to said one side, wherein said sixth means comprises a film cassette holder body means, wherein said holder body means carries a generally planar radiation shield means, wherein said shield means is of a generally L-shaped configuration providing for an opening therethrough of approximately one-quarter the area of the film within said film cassette, said holder body means comprising first retainer means situated generally at one side of said generally planar radiation shield means, second retainer means situated generally at a second side of said generally planar radiation shield means opposite to said one side of said generally planar radiation shield means, and wherein said film cassette may be removably retained between said generally planar radiation shield means and either said first or second retainer means.

29. A cephalostat according to claim 28 and further comprising first keying means carried by said body means, and second keying means carried by said holder body means, said first and second keying means cooperating with each other to determine the location of said holder body means when situated at either said one side of said patient's head or at said other side of said patient's head.

30. A cephalostat according to claim 29 wherein said holder body means further comprises a first plate-like member situated along and operatively against said one side of said generally planar radiation shield means, a second plate-like member situated along and operatively against said second side of said generally planar radiation shield means, securing means operatively securing said first and second plate-like members to each other and thereby tightly containing said radiation shield means therebetween, and wherein said first and second plate-like members are incapable of preventing the passage therethrough of radiation from a source of X-ray radiation.

31. A cephalostat according to claim 30 wherein said first keying means comprises slot-like guide means carried by said body means, and wherein said second keying means comprises a guide member carried by said holder body means and generally extending therefrom as to be slidably cooperatingly received by said slot-like guide means.

* * * * *

UNITED STATES PATENT AND TRADEMARK OFFICE
CERTIFICATE OF CORRECTION

PATENT NO. : 4,579,117

DATED : April 1, 1986

INVENTOR(S) : John L. Spolyar

It is certified that error appears in the above—identified patent and that said Letters Patent is hereby corrected as shown below:

Column 15, line 51, after "spacer" change "4" to --- 404 ---.

Claim 1, line 4 thereof, between "back" and "a" change "or" to --- of ---.

Claim 5, line 10 thereof, immediately after "side" add a comma (,).

Claim 15, line 1 thereof, change "claim 1" to --- claim 14 ---.

Signed and Sealed this

Twenty-sixth Day of August 1986

[SEAL]

Attest:

DONALD J. QUIGG

Attesting Officer

Commissioner of Patents and Trademarks